United States Patent [19]

Fujikawa et al.

[11] Patent Number: 5,055,472
[45] Date of Patent: Oct. 8, 1991

[54] PYRAZOLOPYRIMIDINE TYPE MEVALONOLACTONES

[75] Inventors: Yoshihiro Fujikawa; Mikio Suzuki; Hiroshi Iwasaki, all of Funabashi; Mitsuaki Sakashita; Masaki Kitahara, both of Shiraoka, all of Japan

[73] Assignee: Nissan Chemical Industries, Ltd., Tokyo, Japan

[21] Appl. No.: 426,156

[22] Filed: Oct. 25, 1989

[30] Foreign Application Priority Data

Nov. 14, 1988 [JP] Japan .................. 63-286989
Mar. 15, 1989 [JP] Japan .................... 1-62932
Sep. 8, 1989 [JP] Japan ................... 1-233127

[51] Int. Cl.$^5$ ............... C07D 487/04; A61K 31/505
[52] U.S. Cl. ...................... 514/258; 514/63;
514/267; 544/229; 544/230; 544/250; 544/281;
560/51
[58] Field of Search ............ 544/281, 229, 230;
514/258, 63

[56] References Cited

U.S. PATENT DOCUMENTS 4,178,449 12/1979 Dusza et al. .................. 544/281
4,650,890 3/1987 Jewell et al. .................. 556/446
4,761,419 3/1988 Picard et al. .................. 514/311

FOREIGN PATENT DOCUMENTS 0114027 7/1984 European Pat. Off. .
0217142 4/1987 European Pat. Off. .
0287890 10/1988 European Pat. Off. .

8600307 1/1986 World Int. Prop. O. .
8801997 3/1988 World Int. Prop. O. .

OTHER PUBLICATIONS

Protective Groups in Organic Synthesis by T. H. Greene (John Wiley & Sons, Publ.), pp. 76, 116–118 (1981).

*Primary Examiner*—Mukund J. Shah
*Assistant Examiner*—E. Bernhardt
*Attorney, Agent, or Firm*—Oblon, Spivak, McClelland, Maier & Neustadt

[57] ABSTRACT

The present invention provides a compound of the formula:

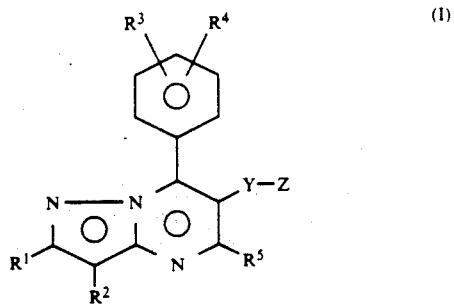

process for their production, pharmaceutical compositions containing them and their pharmaceutical uses, and intermediates useful for their production and processes for the production of such intermediates.

18 Claims, No Drawings

PYRAZOLOPYRIMIDINE TYPE MEVALONOLACTONES

The present invention relates to novel, mevalonolactones having a pyrazolopyrimidine ring, processes for their production, pharmaceutical compositions containing them and their pharmaceutical uses particularly as hypolipoproteinemic and anti-atherosclerotic agents, and intermediates useful for their production and processes for the production of such intermediates.

Some fermentation metabolic products such as compactin, CS-514, Mevinolin or semi-synthetic derivatives or fully synthetic derivatives thereof are known to be inhibitors against HMG-CoA reductase which is a rate limiting enzyme for cholesterol biosynthesis. (A. Endo J. Med Chem., 28(4) 401 (1985)).

CS-514 and Mevinolin have been clinically proved to be potentially useful anti-hyperlipoproteinemic agents, and they are considered to be effective for curing or preventing diseases of coronary arteriosclerosis or atherosclerosis. (IXth Int. Symp. Drugs Affect. Lipid Metab., 1986, Abstract, p30, p31, p66)

However, with respect to fully synthetic derivatives, particularly hetero aromatic derivatives of inhibitors against HMG-CoA reductase, limited information is disclosed in the following literatures:

WPI ACC No. 84-157675, 86-028274, 86-098816, 86-332070, 87-124519, 87-220987, 88-007781, 88-008460, 88-091798, 88-112505, 88-182950, 88-234828, 88-258359, 88-265052, 88-280597, 88-300969, 89-15672, 89-24911, 89-24913, 89-25270, 89-25474, 89-48221, 89-78429.

The present inventors have found that mevalonolactone derivatives having a pyrazolopyrimidine ring, which has not been known, the corresponding dihydroxy carboxylic acids and salts and esters thereof have high inhibitory activities against cholesterol biosynthesis wherein HMG-CoA reductase acts as a rate limiting enzyme. The present invention has been accomplished on the basis of this discovery.

The novel mevalonolactone derivatives of the present invention are represented by the following formula I:

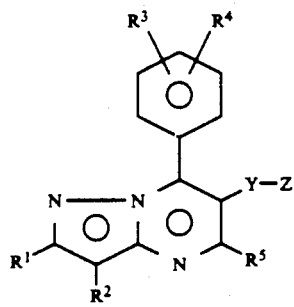

wherein $R^1$ and $R^2$ are independently hydrogen, $C_{1-8}$ alkyl, $C_{2-6}$ alkenyl, $C_{3-7}$ cycloalkyl, $C_{1-6}$ alkoxy, $C_{1-6}$ alkylthio, fluoro, chloro, bromo,

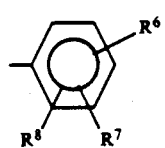

(wherein $R^6$, $R^7$ and $R^8$ are independently hydrogen, $C_{1-4}$ alkyl, $C_{1-3}$ alkoxy, $C_{3-7}$ cycloalkyl, trifluoromethyl, fluoro, chloro or bromo), 2-, 3- or 4-pyridyl, 2- or 5-pyrimidyl, 2- or 3-thienyl, 2- or 3-furyl, α- or β-naphthyl,

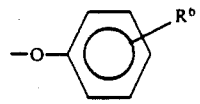

(wherein $R_6$ is as defined above), $-NR^9R^{10}$ (wherein $R^9$ and $R^{10}$ are independently hydrogen, $C_{1-4}$ alkyl,

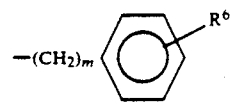

(wherein $R^6$ is as defined above, and m is 1, 2 or 3), or $R^9$ and $R^{10}$ together form $-(CH_2)_j-$ (wherein j is 3, 4 or 5)); or $C_{1-3}$ alkyl substituted by

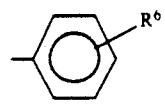

(wherein $R^6$ is as defined above) and by 0, 1 or 2 members selected from the group consisting of $C_{1-8}$ alkyl; or $R^1$ and $R^2$ together form $C_{2-6}$ alkylene unsubstituted or substituted by 1 to 3 members selected from the group consisting of $C_{1-4}$ alkyl, $C_{3-7}$ cycloalkyl, fluoro, chloro and bromo, and by one member selected from the group consisting of

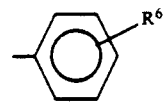

(wherein $R^6$ is as defined above), or $-(CHR^{23})_k-A-(CHR^{24})_l-$ (wherein k and l are respectively 0, 1, 2 or 3, and A is $-C(R^{18})=C(R^{19})-$ (wherein $R^{18}$ and $R^{19}$ are independently hydrogen or $C_{1-3}$ alkyl), $-O-$, $-S-$ or $-N(R^{20})-$ (wherein $R^{20}$ is hydrogen, $C_{1-4}$ alkyl or

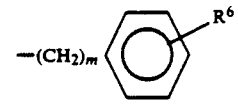

(wherein $R^6$ is as defined above, and m is 1, 2 or 3)), and $R^{23}$ and $R^{24}$ are independently hydrogen or $C_{1-4}$ alkyl), or $-CH=CH-CH=CH-$; $R^3$ and $R^4$ are independently hydrogen, $C_{1-8}$ alkyl, $C_{3-7}$ cycloalkyl, $C_{1-3}$ alkoxy, n-butoxy, i-butoxy, sec-butoxy, t-butoxy, $R^{25}R^{26}N-$ (wherein $R^{25}$ and $R^{26}$ are independently hydrogen or $C_{1-3}$ alkyl), trifluoromethyl, trifluoromethoxy, difluoromethoxy, fluoro, chloro, bromo, phenyl, phenoxy, benzyloxy, hydroxy, trimethylsilyloxy, diphenyl-t-butylsilyloxy, hydroxymethyl or $-O(CH_2)_lOR^{15}$ (wherein $R^{15}$ is hydrogen or $C_{1-3}$ alkyl, and l is 1, 2 or 3); or when located at the ortho position to each other, $R^3$ and $R^4$ may together form $-CH=CH-CH=CH-$ or methylenedioxy; Y is $-CH_2-$, $-CH_2CH_2-$, —CH=CH—, —CH₂—CH=CH—, —CH=CH—CH₂—, —C(CH₃)=CH— or —CH=C(CH₃)—; Z is —Q—CH₂WCH₂—CO₂R¹².

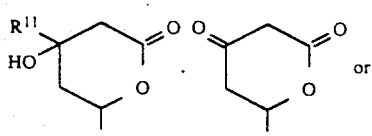

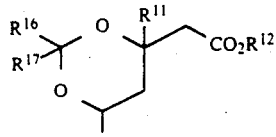

(wherein Q is —C(O)—, —C(OR¹³)₂— or —CH(OH)—; W is —C(O)—, —C(OR¹³)₂— or —C(R¹¹)(OH)—; R¹¹ is hydrogen or C₁₋₃ alkyl; R¹² is hydrogen or R¹⁴ (wherein R¹⁴ is alkyl moiety of chemically or physiologically hydrolyzable alkyl ester or M (wherein M is NHR²⁷R²⁸R²⁹ (wherein R²⁷, R²⁸ and R²⁹ are independently hydrogen or C₁₋₄ alkyl), sodium, potassium or ½ calcium); two R¹³ are independently primary or secondary C₁₋₆ alkyl; or two R¹³ together form —(CH₂)₂— or —(CH₂)₃—; R¹⁶ and R¹⁷ are independently hydrogen or C₁₋₃ alkyl; or R¹⁶ and R¹⁷ together form —(CH₂)₂— or —(CH₂)₃—); and R⁵ is hydrogen, C₁₋₈ alkyl, C₂₋₆ alkenyl, C₃₋₇ cycloalkyl, C₅₋₇ cycloalkenyl, or

(wherein R⁶ is as defined above), or C₁₋₃ alkyl substituted by one member selected from the group consisting of

(wherein R⁶, R⁷ and R⁸ are as defined above) and by 0, 1 or 2 members selected from the group consisting of C₁₋₃ alkyl.

Various substituents in the formula I will be described in detail with reference to specific examples. However, it should be understood that the present invention is by no means restricted by such specific examples.

C₁₋₈ alkyl for R¹, R², R³, R⁴ and R⁵ includes, for example, methyl, ethyl, n-propyl, i-propyl, n-butyl, i-butyl, sec-butyl, t-butyl, n-pentyl, 1,2-dimethylpentyl, n-hexyl, n-heptyl and n-octyl.

C₁₋₄ alkyl for R⁶, R⁷, R⁸, R⁹, R¹⁰, R²⁰, R²³, R²⁴, R²⁷, R²⁸ and R²⁹ includes, for example, methyl, ethyl, n-propyl, i-propyl, n-butyl, i-butyl, sec-butyl and t-butyl.

C₁₋₃ alkyl for R¹¹, R¹⁵, R¹⁶, R¹⁷, R¹⁸, R¹⁹, R²⁵ and R²⁶ includes, for example, methyl, ethyl, n-propyl and i-propyl.

When R¹² is alkyl, R¹⁴ includes methyl, ethyl, n-propyl, i-propyl, c-propyl, n-butyl, i-butyl, sec-butyl, t-butyl, n-pentyl (amyl), i-pentyl and n-hexyl.

C₁₋₆ alkyl for R¹³ includes methyl, ethyl, n-ethyl, n-propyl, i-propyl, n-butyl, i-butyl, sec-butyl, n-pentyl and n-hexyl.

C₃₋₇ cycloalkyl for R¹, R², R³, R⁴, R⁵, R⁶, R⁷ and R⁸ includes, for example, cyclopropyl, 1-methylcyclopropyl, 2-methylcyclopropyl, cyclobutyl, cyclopentyl, cyclohexyl, 4-methylcyclohexyl and cycloheptyl.

C₁₋₆ alkoxy for R¹ and R² includes, for example, methoxy, ethoxy, n-propoxy, i-propoxy, n-butoxy, i-butoxy, sec-butoxy, n-pentyloxy and n-hexyloxy.

C₁₋₃ alkoxy for R³ and R⁴ includes, for example, methoxy, ethoxy, n-propoxy and i-propoxy.

C₁₋₃ alkoxy for R⁶, R⁷ and R⁸ includes, for example, methoxy, ethoxy, n-propoxy and i-propoxy.

C₁₋₆ alkylthio for R¹ and R² includes, for example, methylthio, ethylthio, i-propylthio and n-hexylthio.

C₂₋₆ alkenyl for R¹, R² and R⁵ includes, for example, vinyl, 1-methylvinyl, 1-propenyl, allyl, 1-methyl-1-propenyl, 1-methyl-2-propenyl, 2-methyl-2-propenyl, 2-butenyl, 1-ethylvinyl, 1,2-dimethyl-1-propenyl, 1,2-dimethyl-2-propenyl, 1-ethyl-1-propenyl, 1-ethyl-2-propenyl, 1 methyl-1-butenyl, 1-methyl 2-butenyl, 2-methyl-1-butenyl, 1-i-propylvinyl and 1-methyl 1-pentenyl.

C₅₋₇ cycloalkenyl for R⁵ includes, for example, 2-cyclopentenyl, 2-cyclohexenyl, 2-cycloheptenyl and 4-methyl-2-cyclohexenyl.

M is a metal capable of forming a pharmaceutically acceptable salt and includes, for example, sodium, potassium and ½ calcium. CO₂M includes, for example, —CO₂NH₄ and CO₂H.(primary to tertiary lower alkylamine, for example, triethylamine).

Further, these compounds may have at least one or two asymmetric carbon atoms and may have at least two to four optical isomers. The compounds of the formula I include all of these optical isomers and all of the mixtures thereof.

Among compounds having carboxylic acid moieties falling outside the definition of —CO₂R¹² of the carboxylic acid moiety of substitutent Z of the compounds of the present invention, those which undergo physiological hydrolysis, after intake, to produce the corresponding carboxylic acids (compounds wherein the —CO₂R¹² moiety is —CO₂H) are equivalent to the compounds of the present invention.

Now, preferred substitutents of the compounds of the present invention will be described.

In the following preferred, more preferred, still further preferred and most preferred examples, the numerals for the positions of the substituents indicate the positions on the pyrazolopyrimidine ring.

Preferred compound (1) of the formula I is a compound wherein R¹ and R² are independently hydrogen, C₁₋₈ alkyl, C₂₋₆ alkenyl, C₃₋₇ cycloalkyl, fluoro, chloro, bromo,

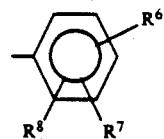

(wherein R⁶, R⁷ and R⁸ are independently hydrogen, C₁₋₄ alkyl, C₁₋₃ alkoxy, C₃₋₇ cycloalkyl, trifluoromethyl, fluoro, chloro or bromo), 2-, 3- or 4-pyridyl, 2- or 5-pyrimidyl, 2- or 3-thienyl, 2- or 3-furyl, α- or β-naphthyl or C₁₋₃ alkyl substituted by

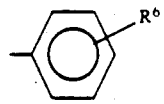

(wherein R$^6$ is as defined above) and by 0, 1 or 2 members selected from the group consisting of C$_{1-8}$ alkyl; or R$^1$ and R$^2$ together form C$_{2-6}$ alkylene unsubstituted or substituted by 1 to 3 members selected from the group consisting of C$_{1-4}$ alkyl, C$_{3-7}$ cycloalkyl, fluoro, chloro or bromo and by one member selected from the group consisting of

(wherein R$^6$ is as defined above) or —(CHR$^{23}$)$_k$—A—(CHR$^{24}$)$_l$—(wherein k and l are independently 0, 1, 2 or 3, A is —C(R$^{18}$)=C(R$^{19}$)—(wherein R$^{18}$ and R$^{19}$ are independently hydrogen or C$_{1-3}$ alkyl), —O—, —S— or —N(R$^{20}$)—(wherein R$^{20}$ is hydrogen, C$_{1-4}$ alkyl or

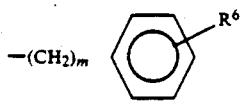

(wherein R$^6$ is as defined above, and m is 1, 2 or 3)) and R$^{23}$ and R$^{24}$ are independently hydrogen or C$_{1-4}$ alkyl or —CH=CH—CH=CH—; R$^3$ and R$^4$ are independently hydrogen, C$_{1-8}$ alkyl, C$_{3-7}$ cycloalkyl, C$_{1-3}$ alkoxy, n-butoxy, i-butoxy, sec-butoxy, t-butoxy, R$^{25}$R$^{26}$N—(wherein R$^{25}$ and R$^{26}$ are independently hydrogen and C$_{1-3}$ alkyl), trifluoromethyl, trifluoromethoxy, difluoromethoxy, fluoro, chloro, bromo, phenyl, phenoxy, benzyloxy, hydroxy, trimethylsilyloxy, diphenyl-t-butylsilyloxy, hydroxymethyl or —O(CH$_2$)$_l$OR$^{15}$ (wherein R$^{15}$ is hydrogen or C$_{1-3}$ alkyl); when located at the ortho position to each other, R$^3$ and R$^4$ together form —CH=CH—CH=CH—or methylenedioxy; Y is —CH$_2$—, —CH$_2$CH$_2$—, —CH=CH— —CH$_2$—CH=CH—, —CH=CH—CH$_2$ , —C(CH$_3$)=CH—or —CH=C(CH$_3$)—; Z is —Q—CH$_2$WCH$_2$—CO$_2$R$^{12}$,

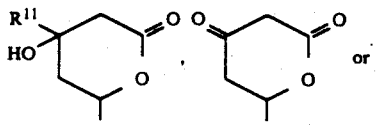 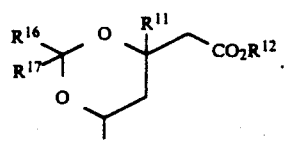

(wherein Q is —C(O)—, —C(OR$^{13}$)$_2$—or —CH(OH)—; W is —C(O)—, —C(OR$^{13}$)$_2$—or —C(R$^{11}$)(OH)—; R$^{11}$ is hydrogen or C$_{1-3}$ alkyl; R$^{12}$ is hydrogen; R$^{14}$ (wherein R$^{14}$ is alkyl moiety of chemically or physiologically hydrolyzable alkyl ester) or M (wherein M is NHR$^{27}$R$^{28}$R$^{29}$ (wherein R$^{27}$, R$^{28}$ and R$^{29}$ are independently hydrogen or C$_{1-4}$ alkyl), sodium, potassium or ½ calcium); two R$^{13}$ are independently primary or secondary C$_{1-6}$ alkyl; or two R$^{13}$ together form —C(CH$_2$)$_2$—or —(CH$_2$)$_3$—; or R$^{16}$ and R$^{17}$ are independently hydrogen or C$_{1-3}$ alkyl; or R$^{16}$ and R$^{17}$ together form —(CH$_2$)$_2$—or —(CH$_2$)$_3$—); R$^5$ is hydrogen, C$_{1-8}$ alkyl, C$_{2-6}$ alkenyl, C$_{3-7}$ cycloalkyl, C$_{5-7}$ cycloalkenyl or

(wherein R$^6$ is as above), or C$_{1-3}$ alkyl substituted by one member selected from the group consisting of

(wherein R$^6$, R$^7$ and R$^8$ are as defined above), and unsubstituted or substituted by 1 or 2 members selected from the group consisting of C$_{1-3}$ alkyl.

More preferred compound (2) of the formula I is a compound wherein R$_1$ and R$^2$ are independently hydrogen, C$_{1-8}$ alkyl, C$_{2-6}$ alkenyl, C$_{3-7}$ cycloalkyl,

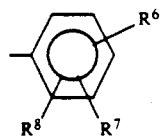

(wherein R$^6$, R$^7$ and R$^8$ are independently hydrogen, C$_{1-4}$ alkyl, C$_{1-3}$ alkoxy, C$_{3-7}$ cycloalkyl, trifluoromethyl, fluoro, chloro or bromo), 2-, 3 or 4-pyridyl, 2- or 5-pyrimidyl, 2- or 3-thienyl, 2- or 3 furyl, α- or β-naphthyl or C$_{1-3}$ alkyl substituted by

(wherein R$^6$ is as defined above) and by 0, 1 or 2 members selected from the group consisting of C$_{1-8}$ alkyl; or R$^1$ and R$^2$ together form C$_{2-6}$ alkylene unsubstituted or substituted by 1 to 3 members selected form the group consisting of C$_{1-4}$ alkyl, C$_{3-7}$ cycloalkyl, fluoro, chloro and bromo, and by one member selected from the group consisting of

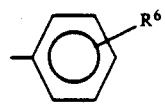

(wherein R$^6$ is as defined above); R$^3$ and R$^4$ are independently hydrogen, C$_{1-8}$ alkyl, C$_{1-3}$ alkoxy, n-bytoxy, i-butoxy, sec butoxy, t-butoxy, trifluoromethyl, fluoro, chloro, bromo, phenoxy, benzyloxy, hydroxy, trimethylsilyloxy, diphenyl-t-butylsilyloxy, hydroxymethyl or —O(CH$_2$)$_l$OR$^{15}$ (wherein R$^{15}$ is hydrogen, C$_{1-3}$ alkyl, and l is 1, 2 or 3); or when located at the ortho position to each other, R$^3$ and R$^4$ may together form methylenedioxy; Y is —CH₂CH₂— or —CH=CH—; Z is —Q—CH₂WCH₂—CO₂R¹² or

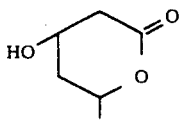

(wherein Q is —C(O)— or —CH(OH)—; W is —C(O)— or —CH(OH)—; and R¹² is as defined with respect to the compound (1)); and R⁵ is C₁₋₈ alkyl, C₂₋₆ alkenyl or cycloalkyl.

Still further preferred compound (3) is a compound wherein R¹ and R² are independently hydrogen, C₁₋₈ alkyl, C₂₋₆ alkenyl, C₃₋₇ cycloalkyl,

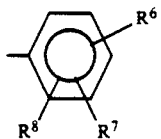

(wherein R⁶, R⁷ and R⁸ are independently hydrogen, C₁₋₄ alkyl, C₁₋₃ alkoxy, C₃₋₇ cycloalkyl, trifluoromethyl, fluoro, chloro or bromo) or C₁₋₃ alkyl unsubstituted or substituted by 1 or 2 members selected from the group consisting of

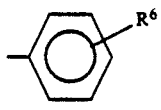

and C₁₋₈ alkyl; or R¹ and R² together form C₂₋₆ alkylene unsubstituted or substituted by 1 to 3 members selected from the group consisting of C₁₋₄ alkyl, C₃₋₇ cycloalkyl, fluoro, chloro and bromo, and by one member selected from the group consisting of

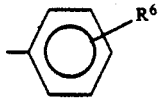

(wherein R⁶ is as defined above) or —(CHR²³)ₖ—A—(CHR²⁴)ₗ—(wherein k and l are independently 0, 1, 2 or 3, A is —C(R¹⁸)=C(R¹⁹)—(wherein R¹⁸ and R¹⁹ are independently hydrogen or C₁₋₃ alkyl), —O—, —S— or —N(R²⁰)—(wherein R²⁰ is hydrogen, C₁₋₄ alkyl or

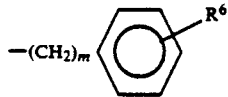

(wherein R⁶ is as defined above, and m is 1, 2 or 3)), and R²³ and R²⁴ are independently hydrogen or C₁₋₄ alkyl) or —CH=CH—CH=CH—; R³ and R⁴ are independently hydrogen, C₁₋₈ alkyl, fluoro, chloro or bromo, and they are located at the 3- and 4-position; Y and Z are as defined with respect to the compound (2); and R⁵ is ethyl, n-propyl, i-propyl or cyclopropyl.

The most preferred compound (4) is a compound wherein R¹ and R² are independently hydrogen, methyl, ethyl, n-propyl, i-propyl, n-butyl, i-butyl, sec-butyl, t-butyl, n-pentyl, i-pentyl, 1,2-dimethylpentyl, n-hexyl, vinyl, n-propenyl, i-propenyl, cyclopropyl, cyclobutyl, cyclohexyl, phenyl, 2-methylphenyl, 3-methylphenyl, 4-methylphenyl, 2-chlorophenyl, 3-chlorophenyl, 4-chlorophenyl, 2-methoxyphenyl, 3-methoxyphenyl, 4-methyoxyphenyl, 3,4-dimethylphenyl, 3,4-dichlorophenyl, 3-trifluoromethylphenyl, benzyl, 4-chlorobenzyl, 4-methylbenzyl, 4-methoxybenzyl, 2-phenethyl; or R¹ and R² together form ethylene, trimethylene, tetramethylene, pentamethylene, hexamethylene, 1-methyltetramethylene, 2-methyltetramethylene, 1-phenyltetramethylene, 2-phenyltetramethylene, 1-chlorotetramethylene, 2-chlorotetramethylene; when R⁴ is hydrogen, R³ is hydrogen, 3-methyl, 4-methyl, 3-chloro, 4 chloro, 3-fluoro or 4-fluoro; or R³ and R⁴ together form 3-methyl-4-chloro, 3,5-dichloro, 3,5-difluoro, 3,5-dimethyl or 3-methyl-4-fluoro; Y and Z are, as defined with respect to the compound (2); and R⁵ is i-propyl or cyclopropyl.

Now, particularly preferred specific compounds of the present invention will be presented.

(a) (E)-7-[7'-(4''-fluorophenyl)—2'-methyl-5'-(1''-methylethyl)pyrazolo[1,5-a]pyrimidin 6'-yl]-3,5-dihydroxyhept-6-enoic acid, a sodium salt, methyl ester, ethyl ester, n-propyl ester or i-propyl ester of the carboxylic acid, or a lactone formed by the condensation of the carboxylic acid with hydroxy at the 5-position (b) (E)-7-[2'-t-butyl-7'-(4''-fluorophenyl) 5'-(1''-methylethyl)pyrazolo1,5-a]pyrimidin-6'-yl]-3,5-dihydroxyhept-6-enoic acid, a sodium salt, methyl ester, ethyl ester, n-propyl ester or i-propyl ester of the carboxylic acid, or a lactone formed by the condensation of the carboxylic acid with hydroxy at the 5-position (c) (E)-7-[7'-(4''-fluorophenyl)—5'-(1''-methylethyl)—2'-phyenylpyrazolo[1,5-a]pyrimidin-6'-yl]-3,5-dihydroxyhept-6-enoic acid, a sodium salt, methyl ester, ethyl ester, n-propyl ester or i-propyl ester of the carboxylic acid, or a lactone formed by the condensation of the carboxylic acid with hydroxy at the 5 position (d) (E)-7-[5'-cyclopropyl-7'-(4''-fluorophenyl)—2'-methylpyrazolol[1,5-a]pyrimidin-6'-yl]-3,5-dihydroxyhept-6-enoic acid, a sodium salt, methyl ester, ethyl ester, n-propyl ester or i-propyl ester of the carboxylic acid, or a lactone formed by the condensation of the carboxylic acid with hydroxy at the 5-position (e) (E)-7-[5'-cyclopropyl-7'-(4''-fluorophenyl)—2',3'-dimethylpyrazolo[1,5-a]pyrimidin-6'-yl]-3,5-dihydroxyhept-6-enoic acid, a sodium salt, methyl ester, ethyl ester, n-propyl ester or i-propyl ester of the carboxylic acid, or a lactone formed by the condensation of the carboxylic acid with hydroxy at the 5-position (f) (E)-7-[5'-cyclopropyl-7'-(4''-fluorophenyl)—2'-methyl-3'-phenylpyrazolo[1,5-a]pyrimidin-6'-yl]-3,5-dihydroxyhept-6-enoic acid, a sodium salt, methyl ester, ethyl ester, n-propyl ester or i-propyl ester of the carboxylic acid, or a lactone formed by the condensation of the carboxylic acid with hydroxy at the 5-position (g) (E)-7-[7'-(4''-fluorophenyl)—2'-(2''-furyl)-5'-(1''-methylethyl)pyrazolo[1,5-a]pyrimidin-6'-yl]-3,5-dihydroxyhept-6-enoic acid, a sodium salt, methyl ester, ethyl ester, n-propyl ester or i-propyl ester of the carboxylic acid, or a lactone formed by the condensation of the carboxylic acid with hydroxy at the 5-position (h) (E)-7-[5'-cyclopropyl-7'-(4"-fluorophenyl)—2'-(1"-methylethyl)pyrazolo[1,5-a]pyrimidin-6'-yl]-3,5-dihydroxyhept-6-enoic acid, a sodium salt, methyl ester, ethyl ester, n-propyl ester or i-propyl ester of the carboxylic acid, or a lactone formed by the condensation of the carboxylic acid with hydroxy at the 5-position (i) (E)-7-[7'-(4"-fluorophenyl)—5'-(1"-methylethyl)-2',3'-tetramethylenepyrazolo[1,5-a]pyrimidin-6'-yl]-3,5-dihydroxyhept-6-enoic acid, a sodium salt, methyl ester, ethyl ester, n-propyl ester or i-propyl ester of the carboxylic acid, or a lactone formed by the condensation of the carboxylic acid with hydroxy at the 5-position The mevalonolactones of the formula I can be prepared by the following reaction scheme.

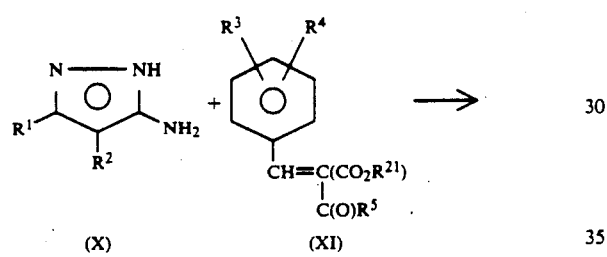

(X) + (XI) →

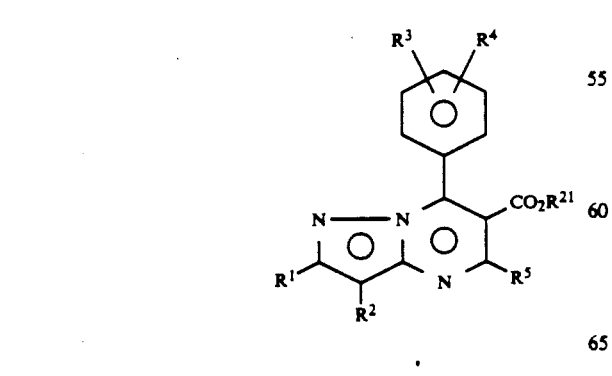

(XII) →

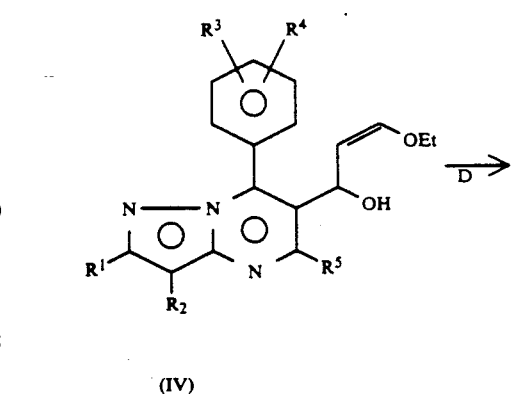

(VII)

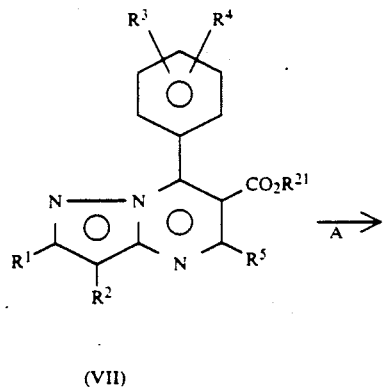

(VII) $\xrightarrow{A}$

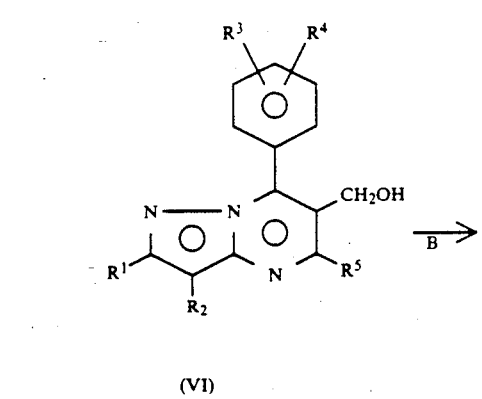

(VI) $\xrightarrow{B}$

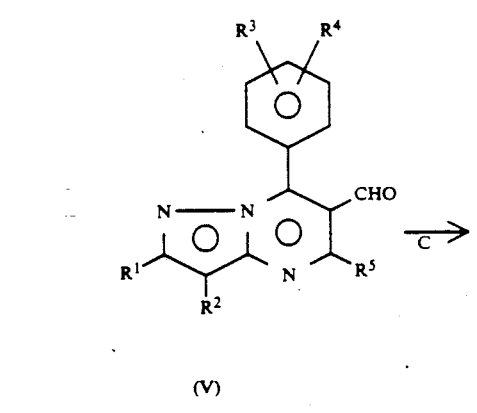

(V) $\xrightarrow{C}$ (IV) $\xrightarrow{D}$

-continued
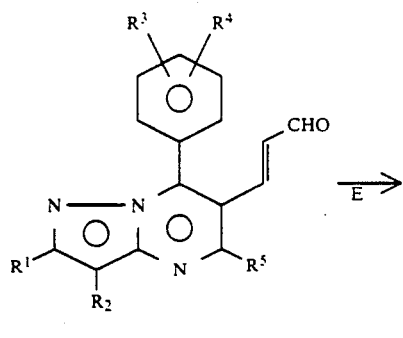
(III)
→ E →
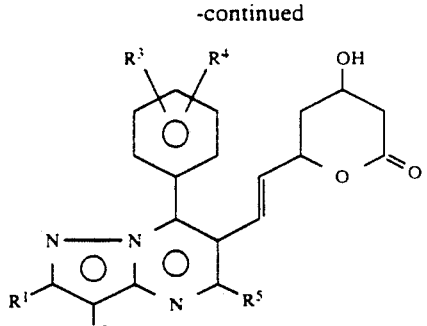
(I-3)
→ J →
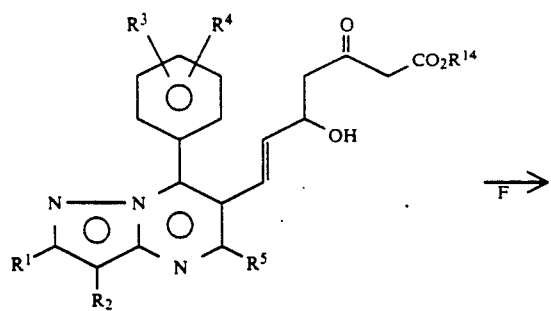
(II)
→ F →
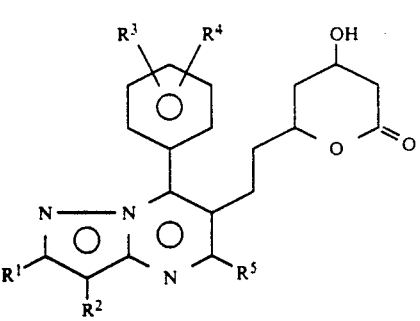
(I-4)
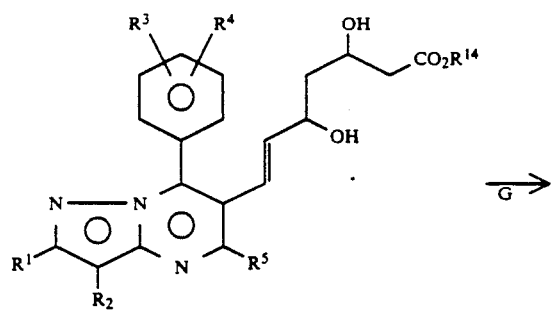
(I-1)
→ G →
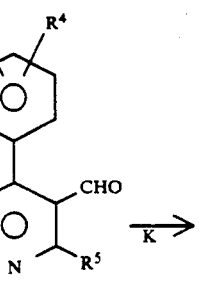
(V)
→ K →
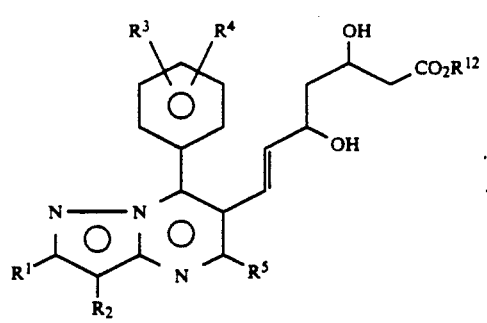
(I-2 (R¹² = H))
(I-5 (R¹² = Na))
→ H →
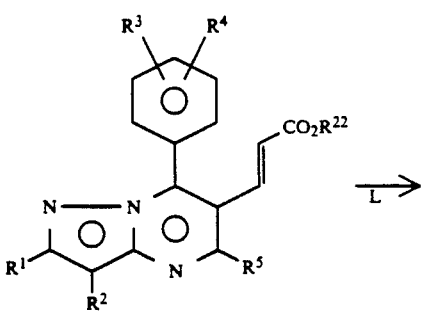
(VIII)
→ L →

-continued
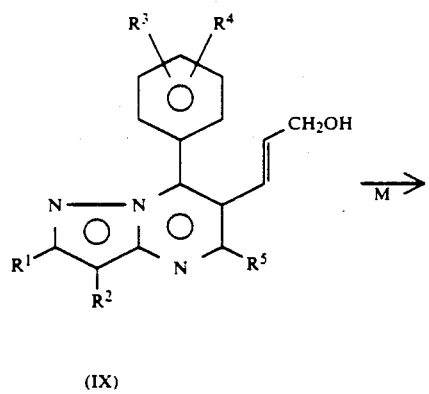
(IX)
M →
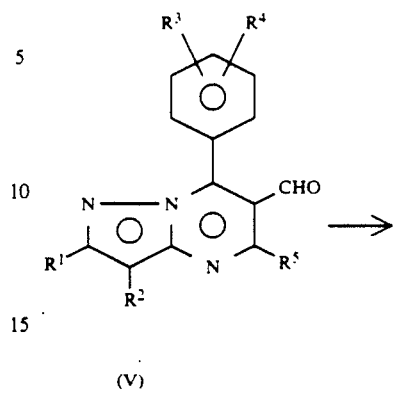
(V)
→
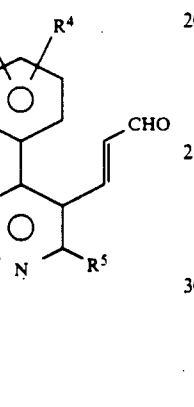
(III)
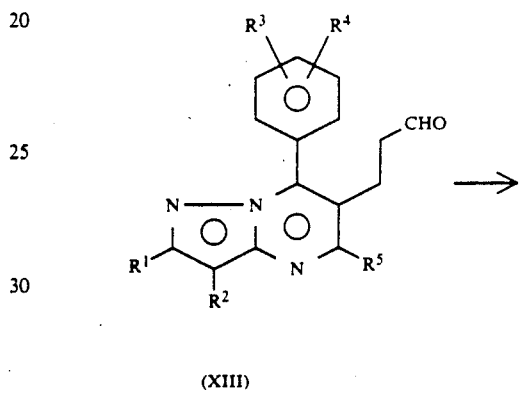
(XIII)
→
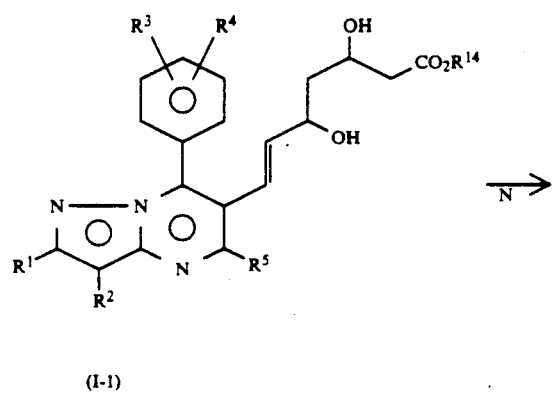
(I-1)
N →
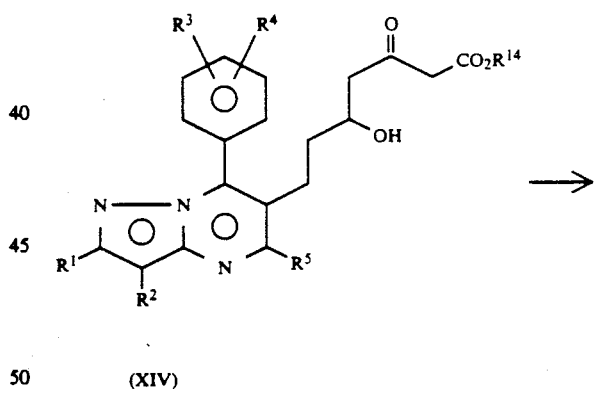
(XIV)
→
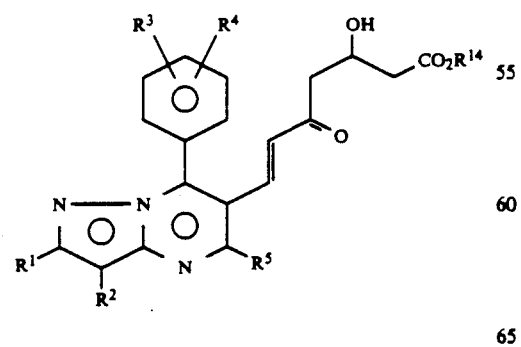
(I-6)
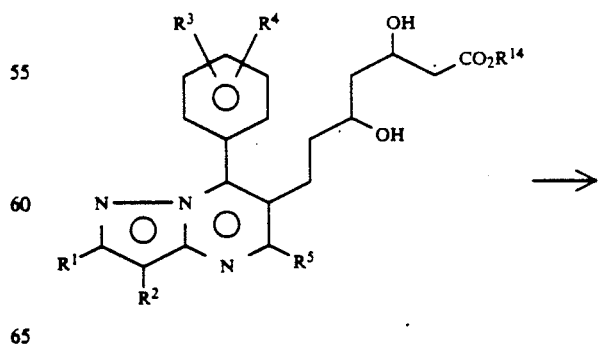
(I-7)
→

-continued
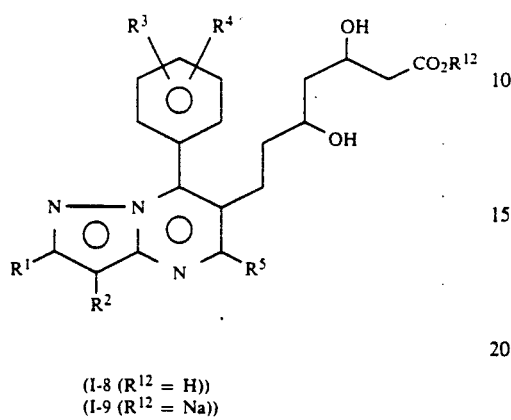
(I-8) ($R^{12}$ = H))
(I-9) ($R^{12}$ = Na))
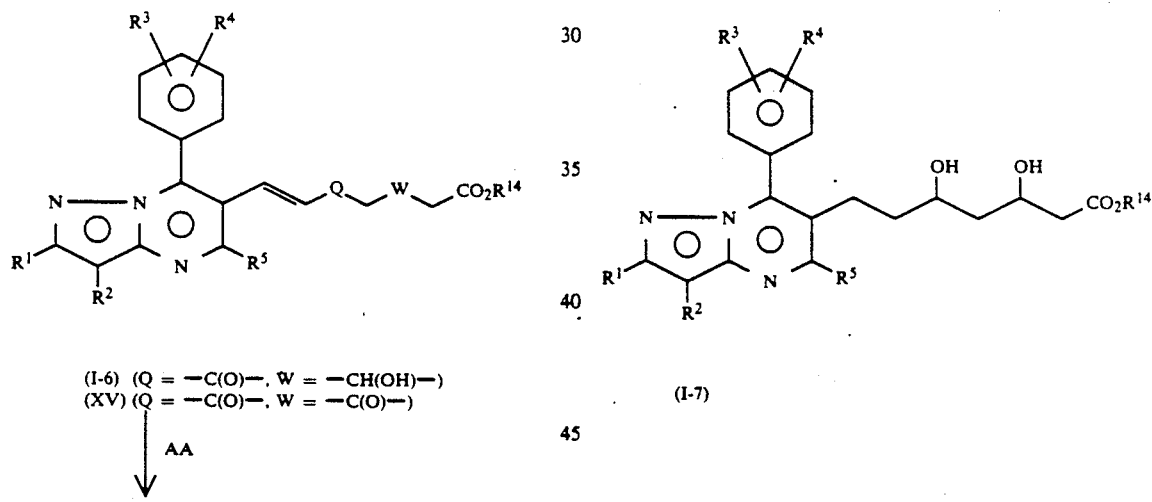
(I-6) (Q = —C(O)—, W = —CH(OH)—)
(XV) (Q = —C(O)—, W = —C(O)—)
↓ AA
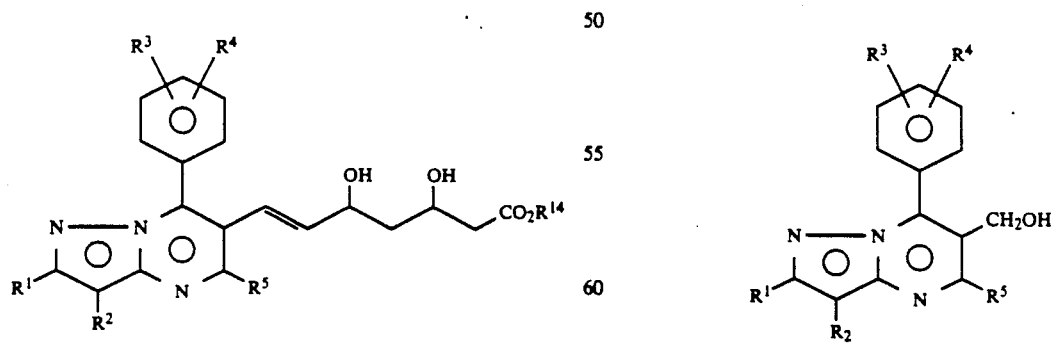
(I-1)
-continued
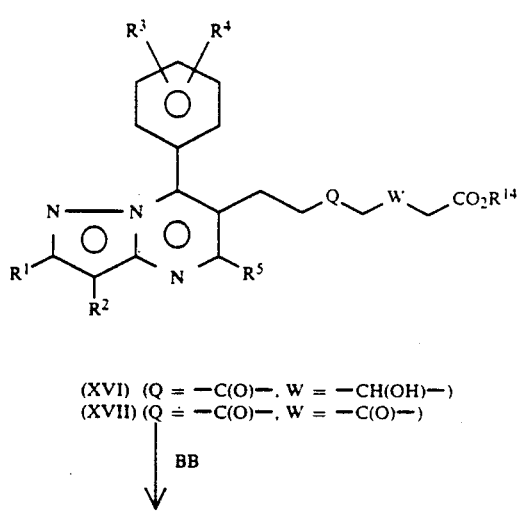
(XVI) (Q = —C(O)—, W = —CH(OH)—)
(XVII) (Q = —C(O)—, W = —C(O)—)
↓ BB
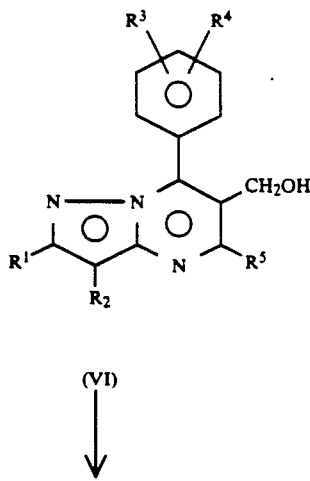
(I-7)
(VI)
↓

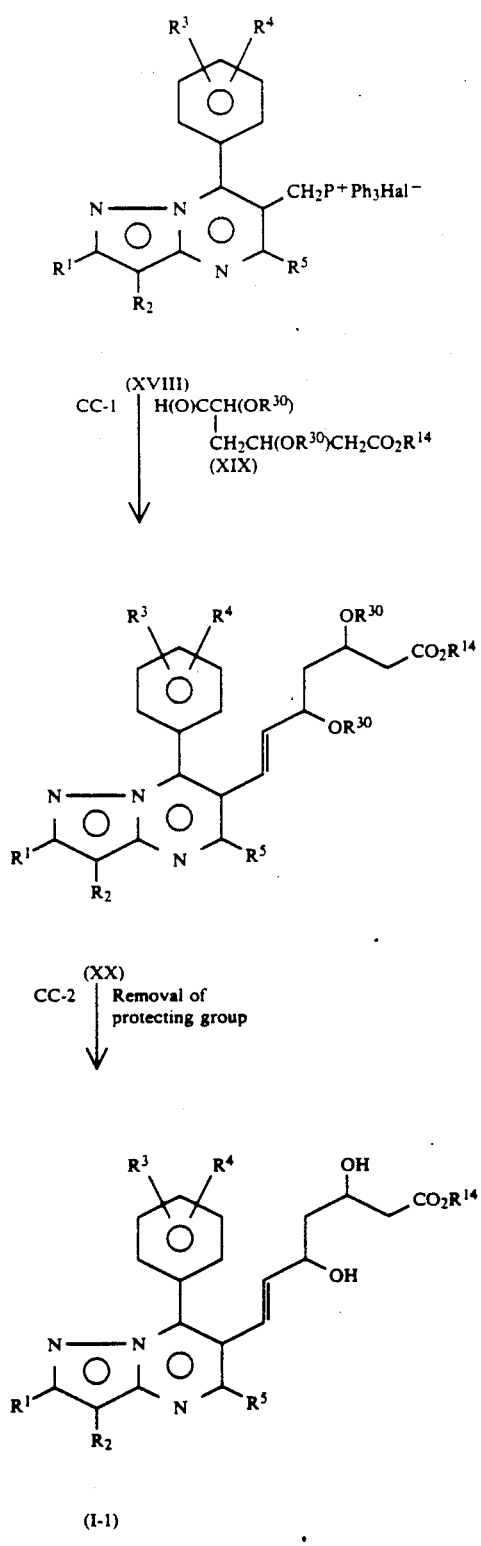
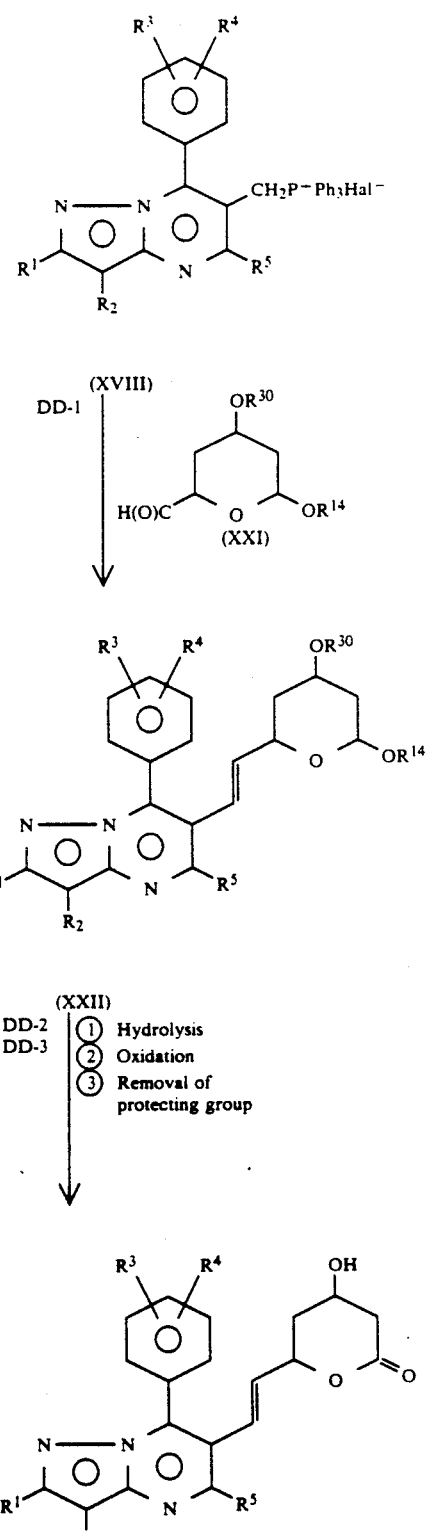

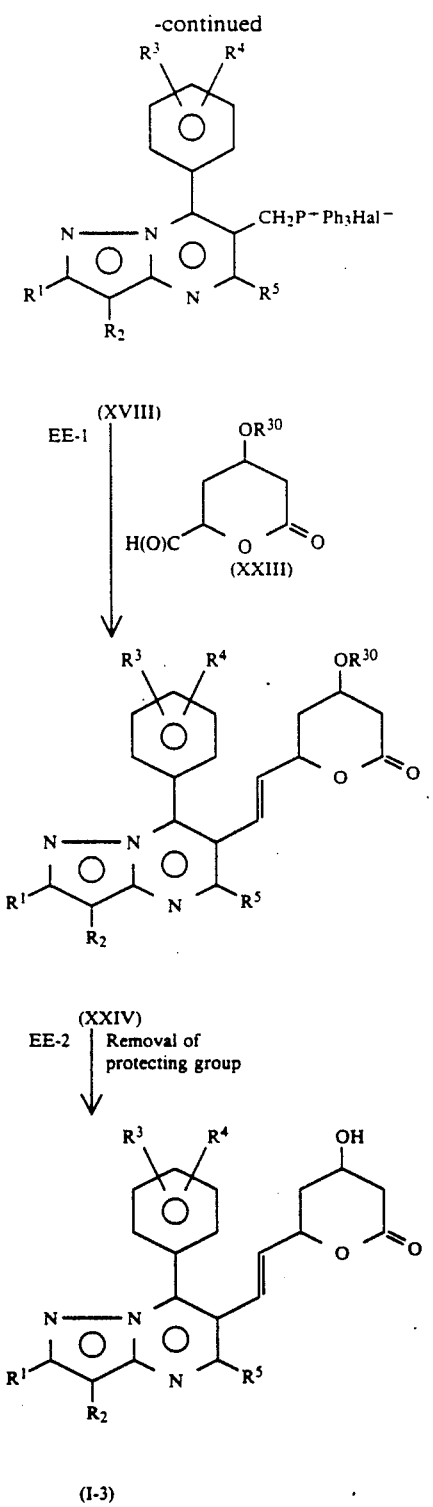

(I-3)

In the above reaction scheme, $R^1$, $R^2$, $R^3$, $R^4$, $R^5$ and $R^{12}$ are as defined above with respect to the formula I, and $R^{21}$ and $R^{22}$ independently represent $C_{1-4}$ lower alkyl such as methyl, ethyl, n-propyl, i-propyl or n-butyl.

The compound of the formula VII can be prepared by oxidizing the compound of the formula XII obtained by reacting the compound of the formula X with the compound of the formula XI (Japanese Unexamined Patent Publications No. 77387/1987 and No. 60985/1988).

Step A represents a reduction reaction of the ester to a primary alcohol. Such reduction reaction can be conducted by using various metal hydrides, preferably diisobutylaluminium hydride, in a solvent such as tetrahydrofuran, toluene or methylene chloride at a temperature of from −20° to 20° C., preferably from −10° to 10° C.

Step B represents an oxidation reaction of the primary alcohol to an aldehyde, which can be conducted by using various oxidizing agents. Preferably, the reaction can be conducted by using pyridinium chlorochromate in methylene chloride at a temperature of from 0° to 25° C., or by using oxalyl chloride, dimethyl sulfoxide and a tertiary amine such as triethylamine (Swern oxidation), or by using a sulfur trioxide pyridine complex.

Step C represents a synthesis of a 3-ethoxy-1-hydroxy-2-propene derivative, which can be prepared by reacting a compound V to a lithium compound which has been preliminarily formed by treating cis-1-ethoxy-2-(tri-n-butylstannyl)ethylene with butyl lithium in tetrahydrofuran.

As the reaction temperature, it is preferred to employ a low temperature at a level of from −60° to −78° C.

Step D represents a synthesis of an enal by acidic hydrolysis. As the acid catalyst, it is preferred to employ p-toluenesulfonic acid, hydrochloric acid or sulfuric acid, and the reaction may be conducted in a solvent mixture of water and tetrahydrofuran or ethanol at a temperature of from 10° to 25° C. The 3-ethoxy-1-hydroxy-2-propene derivative obtained in Step C can be used in Step D without purification i.e. by simply removing tetra-n-butyl tin formed simultaneously.

Step E represents a double anion addition reaction between the enal III and an acetoacetate. Such addition reaction is preferably conducted by using sodium hydride and n-butyl lithium as the base in tetrahydrofuran at a temperature of from −80° to 0° C., preferably from −30° to −10° C.

Step F represents a reduction reaction of the ketocarboxylate of the formula II, by various reducing agents. This reaction comprises reduction of carbonyl by e.g. sodium borohydride, sodium cyanoborohydride, zinc borohydride, disiamylborane, diborane, t-butylaminoborane, pyridine-borane complex, dicyclohexylborane, thexylborane, 9-borabicyclo[3.3.1]nonane, diisopinocamphenyl borane or lithium tri-sec-butyl borohydride to the corresponding dihydroxycarboxylate of the formula I-1.

This reaction can be conducted in a solvent selected from hydrocarbons, halogenated hydrocarbons, $C_{1-4}$ alcohols, ethers and solvent mixtures thereof, at a temperature of from −100° to 50° C., preferably from −78° to 30° C.

Further, as described in J. Amer. Chem. Soc., 105, 593 (1983), a trialkylborane such as tri-n-butylborane or triethylborane and sodium borohydride are used at a low temperature. Further, as described in Tetrahedron Letters, 28, 155 (1987), the erythro form having biologically superior activities can advantageously be obtained by using an alkoxydialkylborane such as methoxydiethylborane or ethoxydiethylborane and sodium borohydride.

This reaction can be conducted by using a solvent mixture of $C_{1-4}$ alcohol and tetrahydrofuran at a temperature of from −80° to −50° C., preferably from −72° to −68° C.

Step G is a step for hydrolyzing the ester. The hydrolysis can be conducted by using an equimolar amount of a base, preferably potassium hydroxide or sodium hydroxide, in a solvent mixture of water and methanol or ethanol at a temperature of from 10° to 25° C. The free acid hereby obtained may be converted to a salt with a suitable base.

Step H is a step for forming a mevalonolactone by the dehydration reaction of the free hydroxy acid I-2. The dehydration reaction can be conducted in benzene or toluene under reflux while removing the resulting water or by adding a suitable dehydrating agent such as molecular sieve.

Further, the dehydration reaction may be conducted in dry methylene chloride by using a lactone-forming agent such as carbodiimide, preferably a water soluble carbodiimide such as N-cyclohexyl-N'-[2'-(methylmorpholinium)ethyl]carbodiimide p-toluene sulfonate at a temperature of from 10° to 35° C., preferably from 20° to 25° C.

Step J represnts a reaction for hydrogenating the double bond connecting the mevalonolactone moiety and the pyrazolopyrimidine ring. This hydrogenation reaction can be conducted by using a catalytic amount of palladium-carbon or rhodium-carbon in a solvent such as methanol, ethanol, tetrahydrofuran or acetonitrile at a temperature of from 0° to 50° C., preferably from 10° to 25° C.

Step K represents a reaction for the synthesis of an $\alpha,\beta$-unsaturated carboxylic acid ester, whereby a transform $\alpha,\beta$-unsaturated carboxylic acid ester can be obtained by a so-called Horner-Wittig reaction by using an alkoxycarbonylmethyl phosphonate. The reaction is conducted by using sodium hydride or potassium t-butoxide as the base in dry tetrahydrofuran at a temperature of from −30° to 0° C., preferably from −20° to −15° C.

Step L represents a reduction reaction of the $\alpha,\beta$-unsaturated carboxylic acid ester to an allyl alcohol. This reduction reaction can be conducted by using various metal hydrides, preferably diisobutylaluminum hydride, in a solvent such as dry tetrahydrofuran or toluene at a temperature of from −10° to 10° C., preferably from −10° to 0° C.

Step M represents an oxidation reaction of the allyl alcohol to an enal. This oxidation reaction can be conducted by using various oxidizing agents, particularly activated manganese dioxide, in a solvent such as tetrahydrofuran, acetone, ethyl ether or ethyl acetate at a temperature of from 0° to 100° C., preferably from 15 to 50° C., or in accordance with Swern oxidation by using oxalyl chloride, dimethylsulfoxide and a tertiary amine such as triethylamine.

Step N represents a reaction for the synthesis of an $\alpha,\beta$-unsaturated ketone by the selective oxidation of the dihydroxy carboxylic acid ester. This reaction can be conducted by using activated manganese dioxide in a solvent such as ethyl ether, tetrahydrofuran, benzene or toluene at a temperature of from 20° to 80° C., preferably from 40° to 80° C.

Further, the compound of the formula I-6 can be prepared from the aldehyde of the formula V by Wadsworth-Emmons coupling reaction (J. Amer. Chem. Soc., 107, 3731 (1985)). It can also be prepared from the enal of the formula III (Tetrahedron Letters, 26, 2951 (1985)).

Further, the compound of the formula I-7 can be prepared by adding a double anion of an acetoacetate to the aldehyde of the formula XIII prepared by the continuous Wittig reaction (WO-8402131) from the aldehyde of the formula V in the same manner as in Step E, to obtain the ketocaroxylate of the formula XIV, and reducing the carbonyl group in the same manner as in Step F.

Step AA represents a reduction reaction of the ketocarboxylate of the formula I-6 or XV by various reducing agents. This reaction comprises reduction of carbonyl by e.g. sodium borohydride, sodium cyanoborohydride, zinc borohydride, disiamylborane, diborane, t-butylaminoborane, pyridine-borane complex, dicyclohexylborane, thexylborane, 9-borabicyclo[3.3.1]nonane, diisopinocamphenyl borane or lithium tri-sec-butyl borohydride to the corresponding dihydroxycarboxylate of the formula I-1.

This reaction can be conducted in a solvent selected from hydrocarbons, halogenated hydrocarbons, $C_{1-4}$ alcohols, ethers and solvent mixtures thereof, at a temperature of from −100° to 50° C., preferably from −78° to 30° C.

Further, as described in J. Amer. Chem. Soc., 105, 593 (1983), a trialkylborane such as tri-n-butylborane or triethylborane and sodium borohydride are used at a low temperature. Further, as described in Tetrahedron Letters, 28, 155 (1987), the erythro form having biologically superior activities can advantageously be obtained by using an alkoxydialkylborane such as methoxydiethylborane or ethoxydiethylborane and sodium borohydride.

This reaction can be conducted by using a solvent mixture of $C_{1-4}$ alcohol and tetrahydrofuran at a temperature of from −80° to −50° C., preferably from −72° to −68° C.

Step BB represents a reaction of reducing the carbonyl group of the ketocarboxylate of the formula XVI or XVII by using various reducing agent to obtain the corresponding dihydroxycarboxylate of the formula I-7. This reaction can be conducted in the same manner as in Step AA.

Substituents $R^1$, $R^2$, $R^3$, $R^4$ and $R^5$ in from the compound of the formula VI which is an intermediate material of the phosphonium compound of the formula XVIII used in Steps CC-1, DD-1, EE-1 and the like, to the compounds of the formula XX, XXII and XXIV, are those defined with respect to the formula I excluding substituents having hydroxyl, amino and monoalkylamino.

Steps CC-1 and CC-2 comprise reacting the compound of the formula XIX with the compound of the formula XVIII (wherein Hal is chlorine, bromine or iodine) by Wittig reaction to obtain the compound of the formula XX, (Step CC-1), followed by hydrolysis of the hydroxyl-protecting group ($R^{30}$) of the compound XX in the presence of a catalyst to obtain the compound of the formual I-1 (Step CC-2).

The phosphonium compound of the formula XVIII can be obtained by halogenating the hydroxyl group of the hydroxymethyl at the 5-position of the pyrazolopyrimidine ring of the compound of the formula VI by a usual method, and then, reacting triphenylphosphine therewith.

The reactions of Steps CC-1 and CC-2 can be conducted in accordance with the method disclosed in Tetrahedron Letters, 25, 2435 (1984), U.S. Pat. No. 4,650,890, EP 0 244 364, etc.

Wittig reaction can be conducted in a dry inert solvent. As the inert solvent, an aliphatic hydrocarbon, toluene or an ether type solvent may be mentioned. Preferred is the ether type solvent, such as diethyl ether, 1,2-diethoxyethane, 1,2-dimethoxyethane or tetrahydrofuran.

Wittig reaction can be conducted in a usual manner. A strong base is added to a solution of the phosphonium compound of the formula XVIII within a temperature range which does not affect the substituents of the phosphonium compound, to form the corresponding ylide compound, and then, the aldehyde of the formula XIX is added to the solution to form the desired compound.

As examples of the strong base, sodium hydride and n-butyl lithium may be mentioned, and preferred is n-butyl lithium.

The temperature upon the addition of the strong base is from −40° to 25° C., and the temperature upon the addition of the aldehyde is −35° to 30° C.

The hydroxyl-protecting group ($R^{30}$) of the compound of the formula XIX, XX, XXI, XXII, XXIII or XXIV is tri-substituted silyl, preferably diphenyl-t-butylsilyl, which is usually used as a hydroxyl-protecting group. Preferred is a protecting group which can be removed without decomposition of the ester or the lactone. The solvent used for the removal of the protecting group is an inert solvent such as tetrahydrofuran or methanol. The catalyst used for the removal of the protecting group is one commonly used for the reaction for removal of silyl. For example, a mixture of acetic acid and tetrabutylammonium fluoride in tetrahydrofuran, or hydrochloride in methanol, may be mentioned.

The reaction temperature for the removal of the protecting group is from 20° to 60° C., preferably from 20° to 30° C.

When there are hydroxyl-protecting groups other than $R^{30}$ at the time of the removal of the protecting group, such protecting groups may be removed to form hydroxyls.

Steps DD-1 to DD-3 represent Wittig reaction of the compound of the formula XVIII with the compound of the formula XXI (Step DD-1), followed by hydrolysis of the acetal to form the hemiacetal, by oxidation of the hemiacetal to form the lactone (Step DD-2), and then, by removal of the hydroxyl-protecting group ($R^{30}$) (Step DD-3).

The hydroxyl-protecting group ($R^{30}$) is as defined in Steps CC-1 and CC-2.

The reaction condition for Step DD-1 may be the same as in the method of Step CC-1.

Step DD-2 represents (1) the hydrolysis and (2) the oxidation. The hydrolysis can be conducted in a solvent mixture such as 10% HCl in tetrahydrofuran or acetic acid/water/tetrahydrofuran, preferably acetic acid/water/tetrahydrofuran.

The reaction temperature is from 10° to 100° C., preferably from 20° to 60° C.

The oxidation of the hemiacetal formed by the hydrolysis can be conducted under a mild condition. The reaction condition varies depending upon the type of the oxidizing agent used.

When the oxidizing agent is pyridinium chlorochromate, the reaction temperature is from 20 to 30° C, and the solvent used is halogenated hydrocarbons, preferably methylene chloride.

Swern oxidation is conducted by using a mixture system of oxalyl chloride/dimethylsulfoxide/triethylamine as the oxidizing agent, the reaction temperature is from −60° to −40° C., and the solvent used is a halogenated hydrocarbon, preferaby methylene chloride.

When the oxidizing agent is N-methylmorpholinoxide and dichloro-tris((phenyl)$_3$P)-ruthenium II, the reaction temperature is from 0° to 40° C., preferably from 20° to 30° C., and the solvent is dry dimethylformamide or acetone.

When the oxidizing agent is $AgCO_3$ on Celite, the reaction temperature is from 0° C. to the boiling point of the reaction solution, preferably at most 150° C., and the solvent is benzene, toluene, xylene, etc.

The reaction condition for the removal of the protecting group in Step DD-3 may be the same as in the method of Step CC-2.

Steps EE-1 and EE-2 represent Wittig reaction of the compound of the formula XVIII with the compound of the formula XXIII (Step EE-1) followed by removal of the hydroxyl-protecting group ($R^{30}$) (Step EE-2).

The hydroxyl-protecting group ($R^{30}$) is as defined in Steps CC-1 and CC-2.

The reaction condition for the Step EE-1 may be the same as in the method of Step CC-1.

The reaction condition for removing the protecting group in Step EE-2 may be the same as in the method of Step CC-2.

The compounds of the formulas I-1, I-2, I-3, I-4, I-5, I-6, I-7, I-8, I-9, II, XIV and XVI shown in Table 1, are typical examples of the compounds of the present invention.

In Table 1, and in the following description, n-means mormal, i- means iso, sec- means secondary, t-means tertiary and c- means cyclo. Likewise, Me means methyl, Et means ethyl, Pr means propyl, Bu means butyl, Hex means hexyl and Ph means phenyl.

TABLE 1

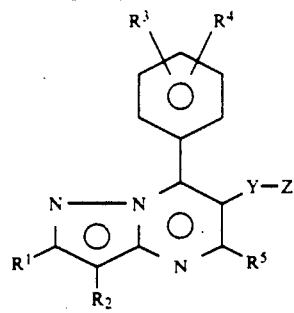

| Compound | −Y−Z |
|---|---|
| (I-1) (R$^{12}$ = Et) | (4,6-dihydroxy-hept-1-enyl)-CO$_2$R$^{12}$ |
| (I-2) (R$^{12}$ = H) | '' |
| (I-3) | 4-hydroxy-6-(prop-1-enyl)-tetrahydropyran-2-one |
| (I-4) | 4-hydroxy-6-propyl-tetrahydropyran-2-one |
| (I-5) (R$^{12}$ = Na) | (4,6-dihydroxy-hept-1-enyl)-CO$_2$R$^{12}$ |
| (I-6) (R$^{12}$ = Et) | (4-oxo-6-hydroxy-hept-1-enyl)-CO$_2$R$^{12}$ |
| (I-7) (R$^{12}$ = Et) | (4,6-dihydroxy-heptyl)-CO$_2$R$^{12}$ |
| (I-8) (R$^{12}$ = H) | (4,6-dihydroxy-heptyl)-CO$_2$R$^{12}$ |
| (I-9) (R$^{12}$ = Na) | (4,6-dihydroxy-heptyl)-CO$_2$R$^{12}$ |
| (II) (R$^{12}$ = Et) | (4-hydroxy-6-oxo-hept-1-enyl)-CO$_2$R$^{12}$ |
| (XIV) (R$^{12}$ = Et) | (4-hydroxy-6-oxo-heptyl)-CO$_2$R$^{12}$ |
| (XVI) (R$^{12}$ = Et) | (4-oxo-6-hydroxy-heptyl)-CO$_2$R$^{12}$ |

| R$^1$ | R$^2$ | R$^3$ | R$^4$ | R$^5$ |
|---|---|---|---|---|
| H | H | H | H | i-Pr |
| H | H | 4-F | H | i-Pr |
| H | H | 4-Cl | H | i-Pr |
| H | H | 3-Me | 4-F | i-Pr |
| H | H | H | H | c-Pr |
| H | H | 4-F | H | c-Pr |
| H | H | 4-Cl | H | c-Pr |

TABLE 1-continued

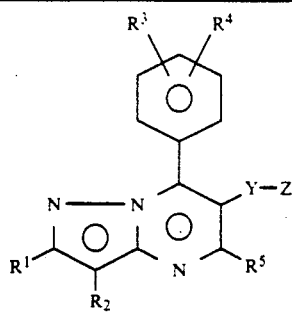

| R¹ | R² | R³ | R⁴ | R⁵ |
|---|---|---|---|---|
| H | H | 3-Me | 4-F | c-Pr |
| Me | H | H | H | i-Pr |
| Me | H | 4-F | H | i-Pr |
| Me | H | 4-Cl | H | i-Pr |
| Me | H | 3-Me | 4-F | i-Pr |
| Me | H | H | H | c-Pr |
| Me | H | 4-F | H | c-Pr |
| Me | H | 4-Cl | H | c-Pr |
| Me | H | 3-Me | 4-F | c-Pr |
| Et | H | H | H | i-Pr |
| Et | H | 4-F | H | i-Pr |
| Et | H | 4-Cl | H | i-Pr |
| Et | H | 3-Me | 4-F | i-Pr |
| Et | H | H | H | c-Pr |
| Et | H | 4-F | H | c-Pr |
| Et | H | 4-Cl | H | c-Pr |
| Et | H | 3-Me | 4-F | c-Pr |
| Et | Me | H | H | i-Pr |
| Et | Me | 4-F | H | i-Pr |
| Et | Me | 4-Cl | H | i-Pr |
| Et | Me | 3-Me | 4-F | i-Pr |
| Et | Me | H | H | c-Pr |
| Et | Me | 4-F | H | c-Pr |
| Et | Me | 4-Cl | H | c-Pr |
| Et | Me | 3-Me | 4-F | c-Pr |
| n-Pr | H | H | H | i-Pr |
| n-Pr | H | 4-F | H | i-Pr |
| n-Pr | H | 4-Cl | H | i-Pr |
| n-Pr | H | 3-Me | 4-F | i-Pr |
| n-Pr | H | H | H | c-Pr |
| n-Pr | H | 4-F | H | c-Pr |
| n-Pr | H | 4-Cl | H | c-Pr |
| n-Pr | H | 3-Me | 4-F | c-Pr |
| i-Pr | H | H | H | i-Pr |
| i-Pr | H | 4-F | H | i-Pr |
| i-Pr | H | 4-Cl | H | i-Pr |
| i-Pr | H | 3-Me | 4-F | i-Pr |
| i-Pr | H | H | H | c-Pr |
| i-Pr | H | 4-F | H | c-Pr |
| i-Pr | H | 4-Cl | H | c-Pr |
| i-Pr | H | 3-Me | 4-F | c-Pr |
| n-Bu | H | H | H | i-Pr |
| n-Bu | H | 4-F | H | i-Pr |
| n-Bu | H | 4-Cl | H | i-Pr |
| n-Bu | H | 3-Me | 4-F | i-Pr |
| n-Bu | H | H | H | c-Pr |
| n-Bu | H | 4-F | H | c-Pr |
| n-Bu | H | 4-Cl | H | c-Pr |
| n-Bu | H | 3-Me | 4-F | c-Pr |
| t-Bu | H | H | H | i-Pr |
| t-Bu | H | 4-F | H | i-Pr |
| t-Bu | H | 4-Cl | H | i-Pr |
| t-Bu | H | 3-Me | 4-F | i-Pr |
| t-Bu | H | H | H | c-Pr |
| t-Bu | H | 4-F | H | c-Pr |
| t-Bu | H | 4-Cl | H | c-Pr |
| t-Bu | H | 3-Me | 4-F | c-Pr |
| c-Pr | H | H | H | i-Pr |
| c-Pr | H | 4-F | H | i-Pr |
| c-Pr | H | 4-Cl | H | i-Pr |
| c-Pr | H | 3-Me | 4-F | i-Pr |
| c-Pr | H | H | H | c-Pr |
| c-Pr | H | 4-F | H | c-Pr |
| c-Pr | H | 4-Cl | H | c-Pr |
| c-Pr | H | 3-Me | 4-F | c-Pr |

TABLE 1-continued

| R1 | R2 | R3 | R4 | R5 |
|---|---|---|---|---|
| H | Ph | H | H | i-Pr |
| H | Ph | 4-F | H | i-Pr |
| H | Ph | 4-Cl | H | i-Pr |
| H | Ph | 3-Me | 4-F | i-Pr |
| H | Ph | H | H | c-Pr |
| H | Ph | 4-F | H | c-Pr |
| H | Ph | 4-Cl | H | c-Pr |
| H | Ph | 3-Me | 4-F | c-Pr |
| Me | Ph | H | H | i-Pr |
| Me | Ph | 4-F | H | i-Pr |
| Me | Ph | 4-Cl | H | i-Pr |
| Me | Ph | 3-Me | 4-F | i-Pr |
| Me | Ph | H | H | c-Pr |
| Me | Ph | 4-F | H | c-Pr |
| Me | Ph | 4-Cl | H | c-Pr |
| Me | Ph | 3-Me | 4-F | c-Pr |
| n-Pr | Ph | H | H | i-Pr |
| n-Pr | Ph | 4-F | H | i-Pr |
| n-Pr | Ph | 4-Cl | H | i-Pr |
| n-Pr | Ph | 3-Me | 4-F | i-Pr |
| n-Pr | Ph | H | H | c-Pr |
| n-Pr | Ph | 4-F | H | c-Pr |
| n-Pr | Ph | 4-Cl | H | c-Pr |
| n-Pr | Ph | 3-Me | 4-F | c-Pr |
| i-Pr | Ph | H | H | i-Pr |
| i-Pr | Ph | 4-F | H | i-Pr |
| i-Pr | Ph | 4-Cl | H | i-Pr |
| i-Pr | Ph | 3-Me | 4-F | i-Pr |
| i-Pr | Ph | H | H | c-Pr |
| i-Pr | Ph | 4-F | H | c-Pr |
| i-Pr | Ph | 4-Cl | H | c-Pr |
| i-Pr | Ph | 3-Me | 4-F | c-Pr |
| PhCH2 | Ph | H | H | i-Pr |
| PhCH2 | Ph | 4-F | H | i-Pr |
| PhCH2 | Ph | 4-Cl | H | i-Pr |
| PhCH2 | Ph | 3-Me | 4-F | i-Pr |
| PhCH2 | Ph | H | H | c-Pr |
| PhCH2 | Ph | 4-F | H | c-Pr |
| PhCH2 | Ph | 4-Cl | H | c-Pr |
| PhCH2 | Ph | 3-Me | 4-F | c-Pr |
| H | 4-F—Ph | H | H | i-Pr |
| H | 4-F—Ph | 4-F | H | i-Pr |
| H | 4-F—Ph | 4-Cl | H | i-Pr |
| H | 4-F—Ph | 3-Me | 4-F | i-Pr |
| H | 4-F—Ph | H | H | c-Pr |
| H | 4-F—Ph | 4-F | H | c-Pr |
| H | 4-F—Ph | 4-Cl | H | c-Pr |
| H | 4-F—Ph | 3-Me | 4-F | c-Pr |
| H | 4-MeO—Ph | H | H | i-Pr |
| H | 4-MeO—Ph | 4-F | H | i-Pr |
| H | 4-MeO—Ph | 4-Cl | H | i-Pr |
| H | 4-MeO—Ph | 3-Me | 4-F | i-Pr |
| H | 4-MeO—Ph | H | H | c-Pr |
| H | 4-MeO—Ph | 4-F | H | c-Pr |
| H | 4-MeO—Ph | 4-Cl | H | c-Pr |
| H | 4-MeO—Ph | 3-Me | 4-F | c-Pr |
| Ph | H | H | H | i-Pr |
| Ph | H | 4-F | H | i-Pr |
| Ph | H | 4-Cl | H | i-Pr |
| Ph | H | 3-Me | 4-F | i-Pr |
| Ph | H | H | H | c-Pr |
| Ph | H | 4-F | H | c-Pr |
| Ph | H | 4-Cl | H | c-Pr |
| Ph | H | 3-Me | 4-F | c-Pr |
| 4-F—Ph | H | H | H | i-Pr |

TABLE 1-continued

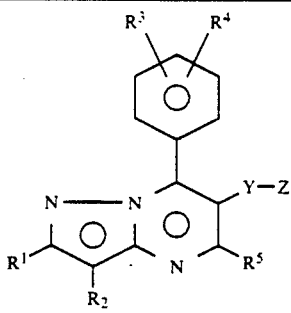

| R1 | R2 | R3 | R4 | R5 |
|---|---|---|---|---|
| 4-F—Ph | H | 4-F | H | i-Pr |
| 4-F—Ph | H | 4-Cl | H | i-Pr |
| 4-F—Ph | H | 3-Me | 4-F | i-Pr |
| 4-F—Ph | H | H | H | c-Pr |
| 4-F—Ph | H | 4-F | H | c-Pr |
| 4-F—Ph | H | 4-Cl | H | c-Pr |
| 4-F—Ph | H | 3-Me | 4-F | c-Pr |
| 4-Cl—Ph | H | H | H | i-Pr |
| 4-Cl—Ph | H | 4-F | H | i-Pr |
| 4-Cl—Ph | H | 4-Cl | H | i-Pr |
| 4-Cl—Ph | H | 3-Me | 4-F | i-Pr |
| 4-Cl—Ph | H | H | H | c-Pr |
| 4-Cl—Ph | H | 4-F | H | c-Pr |
| 4-Cl—Ph | H | 4-Cl | H | c-Pr |
| 4-Cl—Ph | H | 3-Me | 4-F | c-Pr |
| 4-MeO—Ph | H | H | H | i-Pr |
| 4-MeO—Ph | H | 4-F | H | i-Pr |
| 4-MeO—Ph | H | 4-Cl | H | i-Pr |
| 4-MeO—Ph | H | 3-Me | 4-F | i-Pr |
| 4-MeO—Ph | H | H | H | c-Pr |
| 4-MeO—Ph | H | 4-F | H | c-Pr |
| 4-MeO—Ph | H | 4-Cl | H | c-Pr |
| 4-MeO—Ph | H | 3-Me | 4-F | c-Pr |
| Ph | i-Pr | H | H | i-Pr |
| Ph | i-Pr | 4-F | H | i-Pr |
| Ph | i-Pr | 4-Cl | H | i-Pr |
| Ph | i-Pr | 3-Me | 4-F | i-Pr |
| Ph | i-Pr | H | H | c-Pr |
| Ph | i-Pr | 4-F | H | c-Pr |
| Ph | i-Pr | 4-Cl | H | c-Pr |
| Ph | i-Pr | 3-Me | 4-F | c-Pr |
| Ph | Me | H | H | i-Pr |
| Ph | Me | 4-F | H | i-Pr |
| Ph | Me | 4-Cl | H | i-Pr |
| Ph | Me | 3-Me | 4-F | i-Pr |
| Ph | Me | H | H | c-Pr |
| Ph | Me | 4-F | H | c-Pr |
| Ph | Me | 4-Cl | H | c-Pr |
| Ph | Me | 3-Me | 4-F | c-Pr |
| α-naphthyl | Me | H | H | i-Pr |
| α-naphthyl | Me | 4-F | H | i-Pr |
| α-naphthyl | Me | 4-Cl | H | i-Pr |
| α-naphthyl | Me | 3-Me | 4-F | i-Pr |
| α-naphthyl | Me | H | H | c-Pr |
| α-naphthyl | Me | 4-F | H | c-Pr |
| α-naphthyl | Me | 4-Cl | H | c-Pr |
| α-naphthyl | Me | 3-Me | 4-F | c-Pr |
| H | Me | H | H | i-Pr |
| H | Me | 4-F | H | i-Pr |
| H | Me | 4-Cl | H | i-Pr |
| H | Me | 3-Me | 4-F | i-Pr |
| H | Me | H | H | c-Pr |
| H | Me | 4-F | H | c-Pr |
| H | Me | 4-Cl | H | c-Pr |
| H | Me | 3-Me | 4-F | c-Pr |
| H | i-Pr | H | H | i-Pr |
| H | i-Pr | 4-F | H | i-Pr |
| H | i-Pr | 4-Cl | H | i-Pr |
| H | i-Pr | 3-Me | 4-F | i-Pr |
| H | i-Pr | H | H | c-Pr |
| H | i-Pr | 4-F | H | c-Pr |
| H | i-Pr | 4-Cl | H | c-Pr |
| H | i-Pr | 3-Me | 4-F | c-Pr |
| H | n-Hex | H | H | i-Pr |
| H | n-Hex | 4-F | H | i-Pr |

TABLE 1-continued

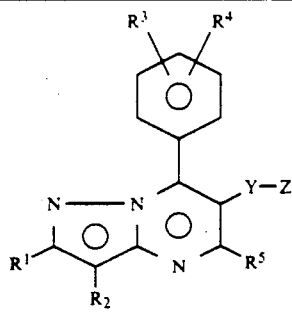

| R¹ | R² | R³ | R⁴ | R⁵ |
|---|---|---|---|---|
| H | n-Hex | 4-Cl | H | i-Pr |
| H | n-Hex | 3-Me | 4-F | i-Pr |
| H | n-Hex | H | H | c-Pr |
| H | n-Hex | 4-F | H | c-Pr |
| H | n-Hex | 4-Cl | H | c-Pr |
| H | n-Hex | 3-Me | 4-F | c-Pr |
| H | vinyl | H | H | i-Pr |
| H | vinyl | 4-F | H | i-Pr |
| H | vinyl | 4-Cl | H | i-Pr |
| H | vinyl | 3-Me | 4-F | i-Pr |
| H | vinyl | H | H | c-Pr |
| H | vinyl | 4-F | H | c-Pr |
| H | vinyl | 4-Cl | H | c-Pr |
| H | vinyl | 3-Me | 4-F | c-Pr |
| Me | Me | H | H | i-Pr |
| Me | Me | 4-F | H | i-Pr |
| Me | Me | 4-Cl | H | i-Pr |
| Me | Me | 3-Me | 4-F | i-Pr |
| Me | Me | H | H | c-Pr |
| Me | Me | 4-F | H | c-Pr |
| Me | Me | 4-Cl | H | c-Pr |
| Me | Me | 3-Me | 4-F | c-Pr |
| i-Pr | Et | H | H | i-Pr |
| i-Pr | Et | 4-F | H | i-Pr |
| i-Pr | Et | 4-Cl | H | i-Pr |
| i-Pr | Et | 3-Me | 4-F | i-Pr |
| i-Pr | Et | H | H | c-Pr |
| i-Pr | Et | 4-F | H | c-Pr |
| i-Pr | Et | 4-Cl | H | c-Pr |
| i-Pr | Et | 3-Me | 4-F | c-Pr |
| 2-furyl | H | H | H | i-Pr |
| 2-furyl | H | 4-F | H | i-Pr |
| 2-furyl | H | 4-Cl | H | i-Pr |
| 2-furyl | H | 3-Me | 4-F | i-Pr |
| 2-furyl | H | H | H | c-Pr |
| 2-furyl | H | 4-F | H | c-Pr |
| 2-furyl | H | 4-Cl | H | c-Pr |
| 2-furyl | H | 3-Me | 4-F | c-Pr |
| 2-thienyl | H | H | H | i-Pr |
| 2-thienyl | H | 4-F | H | i-Pr |
| 2-thienyl | H | 4-Cl | H | i-Pr |
| 2-thienyl | H | 3-Me | 4-F | i-Pr |
| 2-thienyl | H | H | H | c-Pr |
| 2-thienyl | H | 4-F | H | c-Pr |
| 2-thienyl | H | 4-Cl | H | c-Pr |
| 2-thienyl | H | 3-Me | 4-F | c-Pr |
| 2-pyridyl | H | H | H | i-Pr |
| 2-pyridyl | H | 4-F | H | i-Pr |
| 2-pyridyl | H | 4-Cl | H | i-Pr |
| 2-pyridyl | H | 3-Me | 4-F | i-Pr |
| 2-pyridyl | H | H | H | c-Pr |
| 2-pyridyl | H | 4-F | H | c-Pr |
| 2-pyridyl | H | 4-Cl | H | c-Pr |
| 2-pyridyl | H | 3-Me | 4-F | c-Pr |
| 3-pyridyl | H | H | H | i-Pr |
| 3-pyridyl | H | 4-F | H | i-Pr |
| 3-pyridyl | H | 4-Cl | H | i-Pr |
| 3-pyridyl | H | 3-Me | 4-F | i-Pr |
| 3-pyridyl | H | H | H | c-Pr |
| 3-pyridyl | H | 4-F | H | c-Pr |
| 3-pyridyl | H | 4-Cl | H | c-Pr |
| 3-pyridyl | H | 3-Me | 4-F | c-Pr |
| 3-pyridyl | Me | H | H | i-Pr |
| 3-pyridyl | Me | 4-F | H | i-Pr |
| 3-pyridyl | Me | 4-Cl | H | i-Pr |

TABLE 1-continued

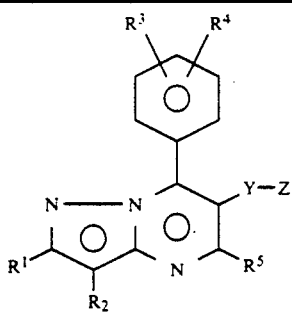

| R¹ | R² | R³ | R⁴ | R⁵ |
|---|---|---|---|---|
| 3-pyridyl | Me | 3-Me | 4-F | i-Pr |
| 3-pyridyl | Me | H | H | c-Pr |
| 3-pyridyl | Me | 4-F | H | c-Pr |
| 3-pyridyl | Me | 4-Cl | H | c-Pr |
| 3-pyridyl | Me | 3-Me | 4-F | c-Pr |
| Me | Cl | H | H | i-Pr |
| Me | Cl | 4-F | H | i-Pr |
| Me | Cl | 4-Cl | H | i-Pr |
| Me | Cl | 3-Me | 4-F | i-Pr |
| Me | Cl | H | H | c-Pr |
| Me | Cl | 4-F | H | c-Pr |
| Me | Cl | 4-Cl | H | c-Pr |
| Me | Cl | 3-Me | 4-F | c-Pr |
| i-Pr | Cl | H | H | i-Pr |
| i-Pr | Cl | 4-F | H | i-Pr |
| i-Pr | Cl | 4-Cl | H | i-Pr |
| i-Pr | Cl | 3-Me | 4-F | i-Pr |
| i-Pr | Cl | H | H | c-Pr |
| i-Pr | Cl | 4-F | H | c-Pr |
| i-Pr | Cl | 4-Cl | H | c-Pr |
| i-Pr | Cl | 3-Me | 4-F | c-Pr |
| Me | SEt | H | H | i-Pr |
| Me | SEt | 4-F | H | i-Pr |
| Me | SEt | 4-Cl | H | i-Pr |
| Me | SEt | 3-Me | 4-F | i-Pr |
| Me | SEt | H | H | c-Pr |
| Me | SEt | 4-F | H | c-Pr |
| Me | SEt | 4-Cl | H | c-Pr |
| Me | SEt | 3-Me | 4-F | c-Pr |
| Me₂N | Me | H | H | i-Pr |
| Me₂N | Me | 4-F | H | i-Pr |
| Me₂N | Me | 4-Cl | H | i-Pr |
| Me₂N | Me | 3-Me | 4-F | i-Pr |
| Me₂N | Me | H | H | c-Pr |
| Me₂N | Me | 4-F | H | c-Pr |
| Me₂N | Me | 4-Cl | H | c-Pr |
| Me₂N | Me | 3-Me | 4-F | c-Pr |
| Vinyl | H | H | H | i-Pr |
| Vinyl | H | 4-F | H | i-Pr |
| Vinyl | H | 4-Cl | H | i-Pr |
| Vinyl | H | 3-Me | 4-F | i-Pr |
| Vinyl | H | H | H | c-Pr |
| Vinyl | H | 4-F | H | c-Pr |
| Vinyl | H | 4-Cl | H | c-Pr |
| Vinyl | H | 3-Me | 4-F | c-Pr |
| Me | OMe | H | H | i-Pr |
| Me | OMe | 4-F | H | i-Pr |
| Me | OMe | 4-Cl | H | i-Pr |
| Me | OMe | 3-Me | 4-F | i-Pr |
| Me | OMe | H | H | c-Pr |
| Me | OMe | 4-F | H | c-Pr |
| Me | OMe | 4-Cl | H | c-Pr |
| Me | OMe | 3-Me | 4-F | c-Pr |
| 3-CF₃—Ph | H | H | H | i-Pr |
| 3-CF₃—Ph | H | 4-F | H | i-Pr |
| 3-CF₃—Ph | H | 4-Cl | H | i-Pr |
| 3-CF₃—Ph | H | 3-Me | 4-F | i-Pr |
| 3-CF₃—Ph | H | H | H | c-Pr |
| 3-CF₃—Ph | H | 4-F | H | c-Pr |
| 3-CF₃—Ph | H | 4-Cl | H | c-Pr |
| 3-CF₃—Ph | H | 3-Me | 4-F | c-Pr |
| α-naphthyl | H | H | H | i-Pr |
| α-naphthyl | H | 4-F | H | i-Pr |
| α-naphthyl | H | 4-Cl | H | i-Pr |
| α-naphthyl | H | 3-Me | 4-F | i-Pr |

TABLE 1-continued

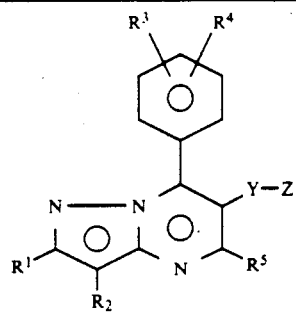

| R¹ | R² | R³ | R⁴ | R⁵ |
|---|---|---|---|---|
| α-naphthyl | H | H | H | c-Pr |
| α-naphthyl | H | 4-F | H | c-Pr |
| α-naphthyl | H | 4-Cl | H | c-Pr |
| α-naphthyl | H | 3-Me | 4-F | c-Pr |
| Me | OPh | H | H | i-Pr |
| Me | OPh | 4-F | H | i-Pr |
| Me | OPh | 4-Cl | H | i-Pr |
| Me | OPh | 3-Me | 4-F | i-Pr |
| Me | OPh | H | H | c-Pr |
| Me | OPh | 4-F | H | c-Pr |
| Me | OPh | 4-Cl | H | c-Pr |
| Me | OPh | 3-Me | 4-F | c-Pr |
| CH₂Ph | H | H | H | i-Pr |
| CH₂Ph | H | 4-F | H | i-Pr |
| CH₂Ph | H | 4-Cl | H | i-Pr |
| CH₂Ph | H | 3-Me | 4-F | i-Pr |
| CH₂Ph | H | H | H | c-Pr |
| CH₂Ph | H | 4-F | H | c-Pr |
| CH₂Ph | H | 4-Cl | H | c-Pr |
| CH₂Ph | H | 3-Me | 4-F | c-Pr |
| 2-Phenethyl | H | H | H | i-Pr |
| 2-Phenethyl | H | 4-F | H | i-Pr |
| 2-Phenethyl | H | 4-Cl | H | i-Pr |
| 2-Phenethyl | H | 3-Me | 4-F | i-Pr |
| 2-Phenethyl | H | H | H | c-Pr |
| 2-Phenethyl | H | 4-F | H | c-Pr |
| 2-Phenethyl | H | 4-Cl | H | c-Pr |
| 2-Phenethyl | H | 3-Me | 4-F | c-Pr |
| H | H | 4-c-Pr | H | i-Pr |
| H | H | 4-c-Pr | H | c-Pr |
| H | H | 4-MeO | H | i-Pr |
| H | H | 4-MeO | H | c-Pr |
| H | H | 4-N(Me)₂ | H | c-Pr |
| H | H | 4-CF₃ | H | c-Pr |
| H | H | 4-Ph | H | c-Pr |
| H | H | 4-OH | H | c-Pr |
| H | H | 4-OCH₂Ph | H | c-Pr |
| H | H | 4-OSiMe₃ | H | c-Pr |
| H | H | 4-CH₂OH | H | c-Pr |
| H | H | 4-OCH₂CH₂OMe | H | c-Pr |
| H | H | 3,4-OCH₂O— | | c-Pr |
| H | H | 3,4-CH=CH—CH=CH | | c-Pr |
| H | H | H | H | H |
| H | H | 4-F | H | H |
| H | H | 4-Cl | H | H |
| H | H | 3-Me | 4-F | H |
| H | H | H | H | Me |
| H | H | 4-F | H | Me |
| H | H | 4-Cl | H | Me |
| H | H | 3-Me | 4-F | Me |
| H | H | H | H | Et |
| H | H | 4-F | H | Et |
| H | H | 4-Cl | H | Et |
| H | H | 3-Me | 4-F | Et |
| H | H | H | H | n-Pr |
| H | H | 4-F | H | n-Pr |
| H | H | 4-Cl | H | n-Pr |
| H | H | 3-Me | 4-F | n-Pr |
| H | H | H | H | n-Hex |
| H | H | 4-F | H | n-Hex |
| H | H | 4-Cl | H | n-Hex |
| H | H | 3-Me | 4-F | n-Hex |
| H | H | H | H | —C(CH₃)=CH₂ |
| H | H | 4-F | H | —C(CH₃)=CH₂ |
| H | H | 4-Cl | H | —C(CH₃)=CH₂ |

TABLE 1-continued

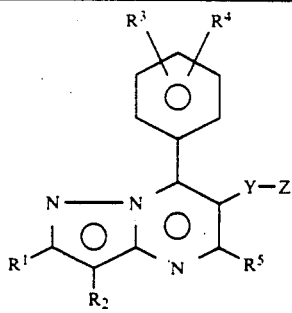

| R1 | R2 | R3 | R4 | Y-Z |
|---|---|---|---|---|
| H | H | 3-Me | 4-F | —C(CH$_3$)═CH$_2$ |
| H | H | H | H | c-Hex |
| H | H | 4-F | H | c-Hex |
| H | H | 4-Cl | H | c-Hex |
| H | H | 3-Me | 4-F | c-Hex |
| H | H | H | H | Cyclo-3-Pentenyl |
| H | H | 4-F | H | Cyclo-3-Pentenyl |
| H | H | 4-Cl | H | Cyclo-3-Pentenyl |
| H | H | 3-Me | 4-F | Cyclo-3-Pentenyl |
| H | H | H | H | Ph |
| H | H | 4-F | H | Ph |
| H | H | 4-Cl | H | Ph |
| H | H | 3-Me | 4-F | Ph |
| H | H | H | H | CH$_2$Ph |
| H | H | 4-F | H | CH$_2$Ph |
| H | H | 4-Cl | H | CH$_2$Ph |
| H | H | 3-Me | 4-F | CH$_2$Ph |

| R1-R2 | R3 | R4 | R5 |
|---|---|---|---|
| (CH$_2$)$_2$CH(Me)CH$_2$ | H | H | i-Pr |
| (CH$_2$)$_2$CH(Me)CH$_2$ | 4-F | H | i-Pr |
| (CH$_2$)$_2$CH(Me)CH$_2$ | 4-Cl | H | i-Pr |
| (CH$_2$)$_2$CH(Me)CH$_2$ | 3-Me | 4-F | i-Pr |
| (CH$_2$)$_2$CH(Me)CH$_2$ | H | H | c-Pr |
| (CH$_2$)$_2$CH(Me)CH$_2$ | 4-F | H | c-Pr |
| (CH$_2$)$_2$CH(Me)CH$_2$ | 4-Cl | H | c-Pr |
| (CH$_2$)$_2$CH(Me)CH$_2$ | 3-Me | 4-F | c-Pr |
| (CH$_2$)$_2$OCH$_2$ | H | H | i-Pr |
| (CH$_2$)$_2$OCH$_2$ | 4-F | H | i-Pr |
| (CH$_2$)$_2$OCH$_2$ | 4-Cl | H | i-Pr |
| (CH$_2$)$_2$OCH$_2$ | 3-Me | 4-F | i-Pr |
| (CH$_2$)$_2$OCH$_2$ | H | H | c-Pr |
| (CH$_2$)$_2$OCH$_2$ | 4-F | H | c-Pr |
| (CH$_2$)$_2$OCH$_2$ | 4-Cl | H | c-Pr |
| (CH$_2$)$_2$OCH$_2$ | 3-Me | 4-F | c-Pr |
| (CH$_2$)$_4$ | H | H | i-Pr |
| (CH$_2$)$_4$ | 4-F | H | i-Pr |
| (CH$_2$)$_4$ | 4-Cl | H | i-Pr |
| (CH$_2$)$_4$ | 3-Me | 4-F | i-Pr |
| (CH$_2$)$_4$ | H | H | c-Pr |
| (CH$_2$)$_4$ | 4-F | H | c-Pr |
| (CH$_2$)$_4$ | 4-Cl | H | c-Pr |
| (CH$_2$)$_4$ | 3-Me | 4-F | c-Pr |
| (CH$_2$)$_3$ | H | H | i-Pr |
| (CH$_2$)$_3$ | 4-F | H | i-Pr |
| (CH$_2$)$_3$ | 4-Cl | H | i-Pr |
| (CH$_2$)$_3$ | 3-Me | 4-F | i-Pr |
| (CH$_2$)$_3$ | H | H | c-Pr |
| (CH$_2$)$_3$ | 4-F | H | c-Pr |
| (CH$_2$)$_3$ | 4-Cl | H | c-Pr |
| (CH$_2$)$_3$ | 3-Me | 4-F | c-Pr |
| (CH$_2$)$_5$ | H | H | i-Pr |
| (CH$_2$)$_5$ | 4-F | H | i-Pr |
| (CH$_2$)$_5$ | 4-Cl | H | i-Pr |
| (CH$_2$)$_5$ | 3-Me | 4-F | i-Pr |
| (CH$_2$)$_5$ | H | H | c-Pr |
| (CH$_2$)$_5$ | 4-F | H | c-Pr |
| (CH$_2$)$_5$ | 4-Cl | H | c-Pr |
| (CH$_2$)$_5$ | 3-Me | 4-F | c-Pr |
| (CH$_2$)$_2$CH(Cl)CH$_2$ | H | H | i-Pr |
| (CH$_2$)$_2$CH(Cl)CH$_2$ | 4-F | H | i-Pr |
| (CH$_2$)$_2$CH(Cl)CH$_2$ | 4-Cl | H | i-Pr |
| (CH$_2$)$_2$CH(Cl)CH$_2$ | 3-Me | 4-F | i-Pr |
| (CH$_2$)$_2$CH(Ph)CH$_2$ | H | H | i-Pr |
| (CH$_2$)$_2$CH(Ph)CH$_2$ | 4-F | H | i-Pr |

TABLE 1-continued

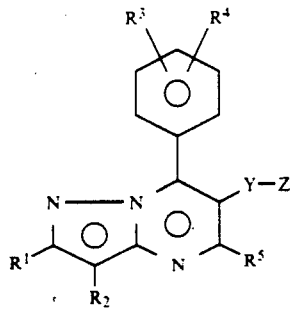

| | | | |
|---|---|---|---|
| (CH₂)₂CH(Ph)CH₂ | 4-Cl | H | i-Pr |
| (CH₂)₂CH(Ph)CH₂ | 3-Me | 4-F | i-Pr |
| (CH₂)₂N(Me)CH₂ | H | H | i-Pr |
| (CH₂)₂N(Me)CH₂ | 4-F | H | i-Pr |
| (CH₂)₂N(Me)CH₂ | 4-Cl | H | i-Pr |
| (CH₂)₂N(Me)CH₂ | 3-Me | 4-F | i-Pr |
| CH₂CH=CHCH₂ | H | H | c-Pr |
| CH₂CH=CHCH₂ | 4-F | H | c-Pr |
| CH₂CH=CHCH₂ | 4-Cl | H | c-Pr |
| CH₂CH=CHCH₂ | 3-Me | 4-F | c-Pr |
| CH=CH—CH=CH | H | H | i-Pr |
| CH=CH—CH=CH | 4-F | H | i-Pr |
| CH=CH—CH=CH | 4-Cl | H | i-Pr |
| CH=CH—CH=CH | 3-Me | 4-F | i-Pr |

Further, pharmaceutically acceptable salts such as potassium salts, ½ calcium salts, esters such as methyl ester, n-propyl ester, i-propyl ester, c-propyl ester, n-butyl ester, i-butyl ester, sec-butyl ester, t-butyl ester, n-pentyl ester, i-pentyl ester and n-hexyl ester, or ammonium salts or trimethylamine salts of these compounds can be prepared in the same manner.

The compounds of the present invention exhibit high inhibitory activities against the cholesterol biosynthesis wherein HMG-CoA reductase acts as a rate limiting enzyme, as shown by the test results given hereinafter, and thus are capable of suppressing or ruducing the amount of cholesterol in blood as lipoprotein. Thus, the compounds of the present invention are useful as curing agents against hyperlipidemia, hyperlipoproteinemia and atheroscleosis.

They may be formulated into various suitable formulations depending upon the manner of the administration. The compounds of the present invention may be administered in the form of free acids or in the form of physiologically hydrolyzable and acceptable esters or lactones, or pharmaceutically acceptable salts.

The pharmaceutical composition of the present invention is preferably administered orally in the form of the compound of the present invention by itself or in the form of powders, granules, tablets or capsules formulated by mixing the compound of the present invention with a suitable pharmaceutically acceptable carrier including a binder such as hydroxypropyl cellulose, syrup, gum arabic, gelatin, sorbitol, tragacanth gum, polyvinyl pyrrolidone or CMC-Ca, an excipient such as lactose, sugar, corn starch, calcium phosphate, sorbitol, glycine or crystal cellulose powder, a lubricant such as magnesium stearate, talc, polyethylene glycol or silica, and a disintegrator such as potato starch.

However, the pharmaceutical composition of the present invention is not limited to such oral administration and it is applicable for parenteral administration. For example, it may be administered in the form of e.g. a suppository formulated by using oily base material such as cacao ,butter, polyethylene glycol, lanolin or fatty acid triglyceride, a transdermal therapeutic base formulated by using liquid paraffin, white vaseline, a higher alcohol, Macrogol ointment, hydrophilic ointment or hydro-gel base material, an injection formulation formulated by using one or more materials selected from the group consisting of polyethylene glycol, hydro-gel base material, distilled water, distilled water for injection and an excipient such as lactose or corn starch, or a formulation for administration through mucous memberanes such as an ocular mucous membrane, a nasal mucous membrane and an oral mucous membrane.

Further, the compounds of the present invention may be combined with basic ion-exchange resins which are capable of binding bile acids and yet not being absorbed by the gastrointestinal tract.

The daily dose of the compound is from 0.05 to 500 mg, preferably from 0.5 to 50 mg, for an adult. It is administered from once to three times per day. The dose may of course be varied depending upon the age, the weight or the condition of illness of the patient.

The compounds of the formulas II to IX are novel, and they are important intermediates for the preparation of the compounds of the formula I. Accordingly, the present invention relates also to the compounds of the formulas II to IX and the processes for their production.

Now, the present invention will be described in further detail with reference to Test Examples for the pharmacological activities of the compounds of the present invention, their Preparation Examples and formulation Examples. However, it should be understood that the present invention is by no means restricted by such specific Examples.

PHARMACOLOGICAL TEST EXAMPLES

Test A: Inhibition of cholesterol biosynthesis from acetate in vitro

Enzyme solution was prepared from liver of male Wistar rat billialy connulated and discharged bile for over 24 hours. Liver was cut out at mid-dark and microsome and supernatant fraction which was precipitable with 40-80% of solution of ammonium sulfate (sup fraction) were prepared from liver homogenate according to the modified method of Knauss et. al.; Kuroda, M., et. al., Biochim. Biophys. Acta, 489, 119 (1977). For assay of cholesterol biosynthesis, microsome (0.1 mg protein) and sup fraction (1.0 mg protein) were incubated for 2 hours at 37° C. in 200 μl of the reaction mixture containing ATP; 1 mM, Glutathione; 6 mM, Glucose-1-phosphate; 10 mM, NAD; 0.25 mM, NADP; 0.25 mM, CoA; 0.04 mM and 0.2 mM [2-$^{14}$C]sodium acetate (0.2 μCi) with 4 μl of test compound solution dissolved in water or dimethyl sulfoxide. To stop reaction and saponify, 1 ml of 15% EtOH-KOH was added to the reactions and heated at 75° C. for 1 hour. Nonsaponifiable, lipids were extracted with petroleum ether and incorporated $^{14}$C radioactivity was counted. Inhibitory activity of compounds was indicated with IC50.

Test B: Inhibition of cholesterol biosynthesis in culture cells

Hep G2 cells at over 5th passage were seeded to 12 well plates and incubated with Dulbecco's modified Eagle (DME) medium containing 10% of fetal bovine serum (FBS) at 37° C., 5% $CO_2$ until cells were confluent for about 7 days. Cells were exposed to the DME medium contaiing 5% of lipoprotein deficient serum (LpDS) prepared by ultracentrifugation method for over 24 hours. Medium was changed to 0.5 ml of fresh 5% LpDS containing DME before assay and 10 μl of test compound solution dissolved in water or DMSO were added. 0.2 μCi of [2-$^{14}$C]sodium acetate (20 μl) was added at 0 hr(B-1) or 4 hrs(B-2) after addition of compounds. After 4 hrs further incubation with [2-$^{14}$C]sodium acetate, medium was removed and cells were washed with phosphate buffered saline (PBS) chilled at 4° C. Cells were scraped with rubber policeman and collected to tubes with PBS and digested with 0.2 ml of 0.5 N KOH at 37° C. Aliquot of digestion was used for protein analysis and remaining was saponified with 1 ml of 15% EtOH-KOH at 75° C. for 1 hour. Nonsaponifiable lipids were extracted with petroleum ether and $^{14}$C radioactivity was counted. Counts were revised by cell protein and indicated with DPM/mg protein. Inhibitory activity of compounds was indicated with IC50.

Test C: Inhibition of cholesterol biosynthesis in vivo

Male Sprague-Dawley rats weighing about 150 g were fed normal Purina chow diet and water ad libitum, and exposed to 12 hours light/12 hours dark lighting pattern (2:00 PM-2:00 AM dark) prior to use for in vivo inhibition test of cholesterol biosynthesis. Animals were separated groups consisting of five rats as to be average mean body weight in each groups. Test compounds at dosage of 0.02-0.2 mg/kg body weight (0.4 ml/100 g body weight), were dissolved in water or suspended in 0.5% methyl cellulose and orally administered at 2-3 hours before mid-dark (8:00 PM), while cholesterol biosynthesis reaches to maximum in rats. As control, rats were orally administered only water or vehicle. At 90 minutes after sample administration, rats were injected intraperitoneally with 10 μCi of [2-$^{14}$C]sodium acetate at volume of 0.2 ml per one. 2 Hours later, blood samples were obtained and serum were separated immediately. Total lipids were extracted according to the method of Folch et al. and saponified with EtOH-KOH. Nonsaponifiable lipids were extracted with petroleum ether and radio activity incorporated into nonsaponifiable lipids was counted.

Inhibitory activity was indicated as percent decrease of counts in testing groups (DPM/2 ml serum/2 hours) from that in control group.

With respect to the compounds of the present invention, the inhibitory activities against the cholesterol biosynthesis in which HMG-CoA reductase serves as a rate limiting enzyme, were measured by the above Test A and B. The results are shown in Tables 2, 3-1 and 3-2.

The chemical structure of Reference Compound is shown as follows.

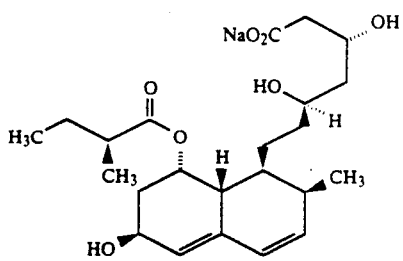

The relative activities of the compounds of the present invention based on the activities of CS-514 by Test A being evaluated to be 1, are shown in Table 2.

TABLE 2

| Relative activities by Test A | |
|---|---|
| Compound of the present invention | Relative activities |
| I-5-1 | 0.64 |
| I-5-2 | 0.09 |
| I-5-3 | 0.27 |
| I-5-4 | 0.39 |
| I-5-5 | 0.29 |
| I-5-6 | 0.75 |
| I-5-7 | 0.20 |
| I-5-8 | 0.09 |
| I-5-9 | 0.13 |

IC$_{50}$ of CS-514 in Test B-1 was 3.66 × 10$^{-8}$ M/l.

The relative activities of the compound o the present invention based on the activities of CS-514 by Test B-1 being evaluated to be 1, are shown in Table 3-1.

TABLE 3-1

| Relative activities by Test B-1 | |
|---|---|
| Compound of the present invention | Relative activities |
| I-1-1 | 17.8 |
| II-2 | 11.0 |
| I-1-3 | 29.5 |
| I-5-3 | 26.0 |

Further, the Test B-1, the inhibitory activities of the compound of the present invention at a concentration of 1.0×10$^{-6}$ mol/l are shown in Table 3-2.

TABLE 3-2

| Inhibitory activities of the compound of the present invention at a concentration of 1.0 × 10⁻⁶ mol/l by Test B-1 | |
|---|---|
| Compound of the present invention | Relative activities |
| I-1-1 | 67.3 |
| I-1-3 | 66.1 |
| I-5-1 | 53.9 |
| I-5-2 | 44.6 |
| I-5-3 | 66.3 |
| I-5-4 | 57.1 |
| I-5-5 | 55.3 |
| I-5-6 | 58.0 |
| II-2 | 58.2 |

Results of the measurement of the inhibitory activities by Test C

The percent decreases of the inhibitory activities by Test C

The percent decreases of counts after the oral administration of 0.2 mg/kg of compound I-5-1 was 50%, relative to the measured value of the control group. The percent decrease of counts after the oral administration of 0.2 mg/kg of CS-514 was 34% under the same condition.

As is evident from the foregoing, the compounds of the present ivention exhibited activities equivalent or superior to the reference compound CS-514 in Tests B-1 and C.

Test D: Acute toxicity

A 0.5% CMC suspension of a test compound was orally administered to ICR male mice (group of three mice). The acute toxicity was determined based on the mortality after seven days. With compound I 5-4 and I-5-6 of the present ivnention, the mortality was 0% even when they were orally administered in an amount of 1,000 mg/kg, respectively.

EXAMPLE 1

Ethyl (E)-7-[7'-(4''-fluorophenyl)-2'-methyl-5'-(1''-methylethyl)pyrazolo[1,5-a]pyrimidin-6'-yl]-3,5-dihydroxyhept-6-enoate (Compound I-1-1)

This compound was prepared by the synthesis comprising the following reaction steps Example 1-a to Example 1-f.

EXAMPLE 1-a 7-(4'-fluorophenyl)-6-hydroxymethyl-2-methyl-5-(1'-methylethyl)pyrazolo[1,5-a]pyrimidin (Compound VI-1)

4.40 g (12.9 mmol) of ethyl 7-(4'-fluorophenyl)-2-methyl-5-(1'-methylethyl)pyrazolo[1,5-a]pyrimidin-6-ylcarboxylate was dissolved in 40 ml of dry toluene under a nitrogen atmosphere and cooled to 0° C. in an ice bath. To this solution, 33 ml of a 16 weight % diisobutylaluminium hydride-toluene solution was dropwise added, and then, the mixture was stirred at 0° C. for one hour. After confirming the complete disappearance of ethyl 7-(4'-fluorophenyl)-2-methyl-5-(1'-methylethyl)pyrazolo[1,5-a]pyrimidin-6-ylcarboxylate by thin layer chromatography, a saturated ammonium chloride aqueous solution was added thereto at 0° C. to terminate the reaction. Diethyl ether was added to the reaction mixture, and the organic layer was separated. The gelled substance was dissolved by an addition of a sodium hydroxide aqueous solution and newly extracted with ethyl ether. The ethyl ether extracts were put together and dried over anhydrous magnesium sulfate. The extract was subjected to filtration, and the solvent was distilled off and the residue was recrystallized from ethyl acetate to obtain 3.24 g (yield: 84%) of the slightly yellow desired compound.

Melting point: 188°-188.5.° C.

EXAMPLE 1-b 7-(4'-fluorophenyl)-2-methyl-5-(1'-methylethyl)pVrazolo[1,5-a]pyrimidin-6-yl]carboxyaldehyde (Compound V-1)

3.54 g (16.4 mmol) of pyridinium chlorochromate, 0.59 g of anhydrous sodium acetate and 3.07 g (10.3 mmol) of Compound VI-1 were suspended in 30 ml of dry dichloromethane. The suspension was stirred at room temperature for 2 hours. Then, the solvent was distilled off under reduced pressure. The desired compound was extracted from the residue thereby obtained with diethyl ether. The ether layers were put together, and the solvent was evaporated under reduced pressure to dryness. The residue thereby obtained was subjected to silica gel column chromatography (eluent: chloroform) to obtain 2.77 g (yield: 91%) of the slightly orange colored desired compound.

Melting point: 194°-197° C.

EXAMPLES 1-c and 1-d (E)-3-[7'-(4''-fluorophenyl)-2'-methyl-5'-(1'''-methylethyl)pyrazolo[1,5-a]pyrimidin 6'-yl]propene aldehyde (Compound III-1)

EXAMPLE I-c 9.79 g (27.2 mmol) of cis 1-ethoxy 2-(tri-n-butylstannyl)ethylene was dissolved in 80 ml of dry tetrahydrofuran, and the solution was cooled to −78° C. under a nitrogen atmosphere., 17.6 ml (27.2 mmol) of a 15 weight % n-butyl lithium-n-hexane solution was dropwise added to this solution. The mixture was stirred for 20 minutes, and then, a solution of 2.69 g (9.1 mmol) of Compound V 1 dissolved in 40 ml of dry tetrahydrofuran was dropwise added thereto. The reaction mixture was stirred at −78° C. for one hour, and then, 20 ml of a saturated ammonium chloride solution was added thereto to terminate the reaction. The organic layer was extracted with diethyl ether. The ether extract was washed with a saturated sodium chloride aqueous solution and dried over anhydrous magensium sulfate. The solvent was distilled off under reduced pressure, and the residue was subjected to liquid separation between n-hexane and acetonitrile. The acetonitrile layer was subjected to distillation under reduced pressure to obtain substantially pure Compound IV-1.

EXAMPLE 1-d

Compound IV-1 obtained in Example 1-c was dissolved in 70 ml of tetrahydrofuran, and 20 ml of water and 3 g of p-toluenesulfonic acid were added thereto. The mixture was stirred at room temperature for 2 hours. The reaction solution was carefully neutralized with a sodium hydroxide aqueous solution. Then, diethyl ether was added thereto, and the extraction was conducted a few times. The extract was washed with a saturated sodium chloride aqueous solution and dried over anhydrous magnesium sulfate. Then, the solvent was distilled off under reduced pressure. The residue was subjected to silica gel column chromatography (eluent: ethanol/chloroform =2/98 (v/v)) to obtain the desired compound as yellow substance.

Quantity: 2.03 g (yield: 69%)
Melting point: 166°–167° C.

EXAMPLE 1-e

Ethyl (E)-7-[7'-(4"-fluorophenyl)-2'-methyl-5'-(1"-methylethyl)pyrazolo[1,5-a]pyrimidin-6'-yl]-5-hydroxy-3-oxohepto-6-enoate (Compound II-1)

1.03 g of 60% sodium hydride was washed with n-hexane, dried under a nitrogen stream and then suspended in 200 ml of dry tetrahydrofuran. The suspension was cooled to −15° C. under a nitrogen atmosphere, and 3.15 ml (24.7 mmol) of ethyl acetoacetate was dropwise added thereto. The mixture was stirred for 15 minutes. Then, 16.1 ml (24.7 mmol) of a 15 weight % (n-butyl lithium-n-hexane solution was dropwise added thereto, and the mixture was stirred for 30 minutes. Further, a solution of 2.00 g (6.2 mmol) of Compound III-1 dissolved in dry tetrahydrofuran was dropwise added thereto, and the mixture was stirred for one hour. 10 ml of a saturated ammonium chloride aqueous solution was added to the reaction mixture at −15° C., and the mixture was extracted three times with diethyl ether. The ether solution was washed with a saturated sodium chloride aqueous solution, dried over anhydrous magnesium sulfate and then evaporated under reduced pressure to dryness. The residue was subjected to silica gel column chromatrography (eluent: ethanol/chloroform=3/97 (v/v)) to obtain 2.80 g (yield: 100%) of the slightly yellow desired compound.

Melting point: 92°–95° C.

EXAMPLE 1-f

Ethyl (E)-7-[7'-(4"-fluorophenyl)-2'-methyl-5'-(1"-methylethyl)pyrazolo[1,5-a]pyrimidin-6'-yl]-3,5-dihydroxyhept-6-enoate (Compound I-1-1)

1.90 g (4.2 mmol) of Compound II-1 was dissolved in 25 ml of ethanol under a nitrogen atmosphere, and the mixture was cooled to 0° C. Then, 740 mg (20 mmol) of sodium borohydride was added thereto, and the mixture was stirred for one hour. The mixture was carefully neutralized by an addition of a 10% hydrochloric acid aqueous solution and then extracted three times with diethyl ether. The diethyl ether solution was washed with a saturated sodium chloride aqueous solution, dried over anhydrous magnesium sulfate and then evaporated under reduced pressure to dryness. The residual oil was subjected to silica gel column chromatography (eluent: ethanol/chloroform =3/97 (v/v)) to obtain the slightly yellow desired product.

Quantity: 1.64 g (yield: 86%),
Melting point: 119°–122° C.

EXAMPLE 2

Sodium (E)-7-[7'-(4"-fluorophenyl)-2'-methyl-5'-(1"-methylethyl)pyrazolo[1,5-a]pyrimidin-6'-yl]-3,5-dihydroxyhept-6-enoate (Compound I-5-1)

410 mg (0.90 mmol) of Compound I-1-1 was dissolved in 6 ml of ethanol, and 1.80 ml of a 0.5 N sodium hydroxide aqueous solution was dropwise added thereto. The mixture was stirred at room temperature for one hour. Then, ethanol was distilled off under reduced pressure. 4 ml of water was added thereto and extracted with diethyl ether. The aqueous layer was freeze-dried to obtain 370 mg (yield: 91%) of hygroscopic slightly yellow powder.

Melting point: 182°–186° C.

In the same manner as in Example 1-a, Compounds VI-2 to VI-9 were prepared. Physical properties of the compounds thereby obtained are shown in the following Table.

TABLE 2

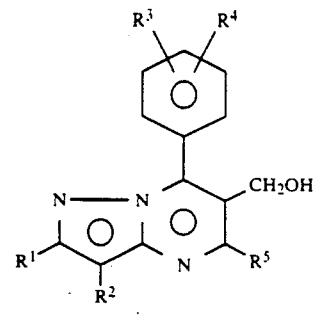

| Compound | $R^1$ | $R^2$ | $R^3$ | $R^4$ | $R^5$ | Melting point (°C.) |
|---|---|---|---|---|---|---|
| VI-2 | t-Bu | H | 4-F | H | i-Pr | 188–191 |
| VI-3 | Ph | H | 4-F | H | i-Pr | 196–198 |
| VI-4 | Me | H | 4-F | H | c-Pr | 203–207 |
| VI-5 | Me | Me | 4-F | H | c-Pr | 174–178 |
| VI-6 | Me | Ph | 4-F | H | c-Pr | 156–159 |
| VI-7 | 2-furyl | H | 4-F | H | i-Pr | 234–235 |
| VI-8 | i-Pr | H | 4-F | H | c-Pr | — |
| VI-9 | —(CH$_2$)$_4$— | | 4-F | H | i-Pr | — |

H-NMR of Compound VI-8 (CDCl$_3$) δ ppm 0.7–1.4(m, 4H), 1.21(d, J=7Hz, 6H), 2.1–2.8(m, 2H), 2.98(Heptalet, J=7Hz, 1H), 4.51(bs, 2H), 6.25(s, 1H), 6.9–7.7(m, 4H)
H-NMR of Compound VI-9 (CDCl$_3$) δ ppm 1.36(d, J=7Hz, 6H), 1.6–2.0(m, 4H), 2.2–3.0(m, 6H), 3.48(Heptalet, J=7Hz, 1H), 4.38(bs, 1H), 6.8–7.7(m, 4H)

In the same manner as in Example 1b, Compounds V-2 to V-9 were prepared. Physical properties of the compounds thereby obtained are shown in the following Table.

TABLE 3

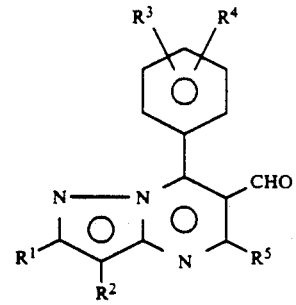

| Compound | $R^1$ | $R^2$ | $R^3$ | $R^4$ | $R^5$ | Melting point (°C.) |
|---|---|---|---|---|---|---|
| V-2 | t-Bu | H | 4-F | H | i-Pr | 103–104 |
| V-3 | Ph | H | 4-F | H | i-Pr | 181–184 |
| V-4 | Me | H | 4-F | H | c-Pr | 193–197 |
| V-5 | Me | Me | 4-F | H | c-Pr | 184–185 |
| V-6 | Me | Ph | 4-F | H | c-Pr | 201–204 |
| V-7 | 2-furyl | H | 4-F | H | i-Pr | 224–225 |
| V-8 | i-Pr | H | 4-F | H | c-Pr | 122–127 |
| V-9 | —(CH$_2$)$_4$— | | 4-F | H | i-Pr | — |

H-NMR of Compound V-9 (CDCl$_3$) δ ppm 1.33(d, J=7Hz, 6H), 1.7–2.0(m, 4H), 2.6–3.0(m, 4H), 4.06(Heptalet, J=7Hz, 1H), 7.0–7.8(m, 4H), 9.75(s, 1H)

In the same manner as in Examples 1-c and 1-d, Compounds III-2 to III-9 were prepared. Physical properties of the compounds thereby obtained are shown in the following Table.

TABLE 4

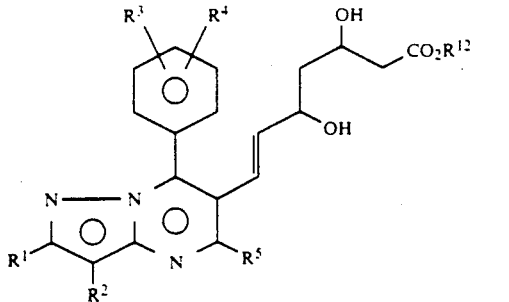

| Compound | R¹ | R² | R³ | R⁴ | R⁵ | Melting point (°C.) |
|---|---|---|---|---|---|---|
| III-2 | t-Bu | H | 4-F | H | i-Pr | 157–159 |
| III-3 | Ph | H | 4-F | H | i-Pr | 199–203 |
| III-4 | Me | H | 4-F | H | c-Pr | 190–193 |
| III-5 | Me | Me | 4-F | H | c-Pr | 205–208 |
| III-6 | Me | Ph | 4-F | H | c-Pr | 202–208 |
| III-7 | 2-furyl | H | 4-F | H | i-Pr | 216–217 |
| III-8 | i-Pr | H | 4-F | H | c-Pr | — |
| III-9 | —(CH$_2$)$_4$— | | 4-F | H | i-Pr | — |

H-NMR of Compound III-8 (CDCl$_3$) δ ppm 0.8–1.4(m, 4H), 1.26(d, J=7Hz, 6H), 2.0–2.4(m, 1H), 3.02(Heptalet, J=7Hz, 1H), 6.30(s, 1H), 6.36(dd, J=16Hz, J=8Hz, 1H), 6.9–7.6(m, 5H), 9.33(d, J=8Hz, 1H)

H-NMR of Compound III-9 (CDCl$_3$) δ ppm 1.33(d, J=7Hz, 6H), 1.7–2.0(m, 4H), 2.6–3.0(m, 4H), 3.32(Heptalet, J=7Hz, 1H), 5.83(dd, J=16Hz, J=8Hz, 1H), 6.9–7.5(m, 5H), 9.29(d, J=8Hz, 1H)

In the same manner as in Example 1-e, Compounds II-2 to II-9 were prepared. Physical properties of the compounds thereby obtained are shown in the following Table.

TABLE 5

| Compound | R¹ | R² | R³ | R⁴ | R⁵ | R¹² | Melting point (°C.) |
|---|---|---|---|---|---|---|---|
| II-2 | t-Bu | H | 4-F | H | i-Pr | Et | 106–109 |
| II-3 | Ph | H | 4-F | H | i-Pr | Et | 123–125 |
| II-4 | Me | H | 4-F | H | c-Pr | Et | 115–117 |
| II-5 | Me | Me | 4-F | H | c-Pr | Et | 129–132 |
| II-6 | Me | Ph | 4-F | H | c-Pr | Et | 119–126 |
| II-7 | 2-furyl | H | 4-F | H | i-Pr | Et | 155–158 |
| II-8 | i-Pr | H | 4-F | H | c-Pr | Et | 78–85 |
| II-9 | —(CH$_2$)$_4$— | | 4-F | H | i-Pr | Et | 163–164 |

In the same manner as in Example 1-f, Compounds I-1-2 to I-1-9 were prepared. Physical properties of the compounds thereby obtained are shown in the following Table.

TABLE 6

| Compound | R¹ | R² | R³ | R⁴ | R⁵ | R¹² | Melting point (°C.) |
|---|---|---|---|---|---|---|---|
| I-1-2 | t-Bu | H | 4-F | H | i-Pr | Et | 120–124 |
| I-1-3 | Ph | H | 4-F | H | i-Pr | Et | 157–158 |
| I-1-4 | Me | H | 4-F | H | c-Pr | Et | Oil |
| I-1-5 | Me | Me | 4-F | H | c-Pr | Et | 131–134 |
| I-1-6 | Me | Ph | 4-F | H | c-Pr | Et | 146–150 |
| I-1-7 | 2-furyl | H | 4-F | H | i-Pr | Et | — |
| I-1-8 | i-Pr | H | 4-F | H | c-Pr | Et | — |
| I-1-9 | —(CH$_2$)$_4$— | | 4-F | H | i-Pr | Et | 153–157 |

H-NMR of Compound I-1-4 (CDCl$_3$) δ ppm 0.9–1.5(m, 5H), 1.29(t, J=7Hz, 3H), 1.6–1.8(m, 1H), 1.9–2.6(m, 3H), 2.39(s, 3H), 2.9–3.3(m, 1H), 3.3–3.8(m, 1H), 3.8–4.5(m, 2H), 4.19(q, J=7Hz, 2H), 5.4–5.7(m, 1H), 6.29(s, 1H), 6.4–6.7(m, 1H), 7.7–7.6(m, 4H)

H-NMR of Compound I-1-7 (CDCl$_3$) δ ppm 0.8–1.0(m, 1H), 1.29(t, J=7Hz, 3H), 1.33(d, J=7Hz, 6H), 1.6–1.8(m, 1H), 2.41(d, J=6Hz, 2H), 3.33(Heptalet, J=7Hz, 1H), 3.4–3.5(m, 1H), 3.7–3.8(m, 1H), 3.9–4.5(m, 2H), 4.19(q, J=7Hz, 2H), 5.35(dd, J=16Hz, J=6Hz, 1H), 6.4–6.6(m, 2H), 6.7–6.9(m, 2H), 7.0–7.3(m, 2H), 7.4–7.6(m, 3H)

H-NMR of Compound I-1-8 (CDCl$_3$) δ ppm 0.9–1.5(m, 8H), 1.26(d, J=7Hz, 6H), 1.6–1.8(m, 1H), 2.1–2.4(m, 1H), 2.43(d, J=6Hz, 2H), 3.04(Heptalet, J=7Hz, 1H), 3.4–3.5(m, 1H), 3.7–3.8(m, 1H), 4.0–4.5(m, 2H), 4.19(q, J=7Hz, 2H), 5.52(dd, J=16Hz, J=6Hz, 1H), 6.33(s, 1H), 6.54(dd, J=6Hz, J=1Hz, 1H), 7.0–7.3(m, 2H), 7.4–7.6(m, 2H)

In the same manner as in Example 2, Compounds I-5-2 to I-5-9 were prepared. Physical properties of the compounds thereby obtained are shown in the following Table.

TABLE 7

| Compound | R¹ | R² | R³ | R⁴ | R⁵ | R¹² | Melting point (°C.) |
|---|---|---|---|---|---|---|---|
| I-5-2 | t-Bu | H | 4-F | H | i-Pr | Na | 205–208 |
| I-5-3 | Ph | H | 4-F | H | i-Pr | Na | 182–189 |
| I-5-4 | Me | H | 4-F | H | c-Pr | Na | 212–215 |
| I-5-5 | Me | Me | 4-F | H | c-Pr | Na | 209–214 |
| I-5-6 | Me | Ph | 4-F | H | c-Pr | Na | 213–217 |
| I-5-7 | 2-furyl | H | 4-F | H | i-Pr | Na | 194–199 |
| I-5-8 | i-Pr | H | 4-F | H | c-Pr | Na | 210–215 |
| I-5-9 | —(CH$_2$)$_4$— | | 4-F | H | i-Pr | Na | 210–216 |

FORMULATION EXAMPLE 1

| Tablets | |
|---|---|
| Compound I-5-1 | 1.0 g |
| Lactose | 5.0 g |

-continued

| Tablets | |
|---|---|
| Crystal cellulose powder | 8.0 g |
| Corn starch | 3.0 g |
| Hydroxypropyl cellulose | 1.0 g |
| CMC-Ca | 1.5 g |
| Magnesium stearate | 0.5 g |
| Total | 20.0 g |

The above components were mixed by a usual method and then tabletted to produce 100 sugar coating tablets each containing 10 mg of the active ingredient.

FORMULATION EXAMPLE 2

| Capsules | |
|---|---|
| Compound I-5-1 | 1.0 g |
| Lactose | 3.5 g |
| Crystal cellulose powder | 10.0 g |
| Magnesium stearate | 0.5 g |
| Total | 15.0 g |

The above components were mixed by a usual method and then packed in No. 4 gelatin capsules to obtain 100 capsules each containing 10 mg of the active ingredient.

FORMULATION EXAMPLE 3

| Soft capsules | |
|---|---|
| Compound I-5-1 | 1.00 g |
| PEG (polyethylene glycol) 400 | 3.89 g |
| Saturated fatty acid triglyceride | 15.00 g |
| Peppermint oil | 0.01 g |
| Polysorbate 80 | 0.10 g |
| Total | 20.00 g |

The above components were mixed and packed in No. 3 soft gelatin capsules by a usual method to obtain 100 soft capsules each containing 10 mg of the active ingredient.

FORMULATION EXAMPLE 4

| Ointment | | |
|---|---|---|
| Compound I-5-1 | 1.0 g | (10.0 g) |
| Liquid Paraffin | 10.0 g | (10.0 g) |
| Cetanol | 20.0 g | (20.0 g) |
| White vaseline | 68.4 g | (59.4 g) |
| Ethylparaben | 0.1 g | (0.1 g) |
| l-menthol | 0.5 g | (0.5 g) |
| Total | 100.0 g | |

The above components were mixed by a usual method to obtain a 1% (10%) ointment.

FORMULATION EXAMPLE 5

| Suppository | |
|---|---|
| Compound I-5-1 | 1.0 g |
| Witepsol H15* | 46.9 g |
| Witepsol W35* | 52.0 g |
| Polysorbate 80 | 0.1 g |
| Total | 100.0 g |

*Trademark for triglyceride compound

The above compounds were melt-mixed by a usual method and poured into supository containers, followed by cooling for solidification to obtain 100 suppositories of 1 g each containing 10 mg of the active ingredient.

FORMULATION EXAMPLE 6

| Injection formulation | |
|---|---|
| Compound I-5-1 | 1 mg |
| Distilled water for injection formulation | 5 ml |

The formulation is prepared by dissolving the compound in the distilled water whenever it is required.

FORMULATION 7

| Granules | |
|---|---|
| Compound I-5-1 | 1.0 g |
| Lactose | 6.0 g |
| Crystal cellulose powder | 6.5 g |
| Corn starch | 5.0 g |
| Hydroxypropyl cellulose | 1.0 g |
| Magnesium stearate | 0.5 g |
| Total | 20.0 g |

The above compounds were granulated by a usual method and packaged to obtain 100 packages each containing 200 mg of the granules so that each package contains 10 mg of the active ingredients.

We claim:

1. A compound of the formula

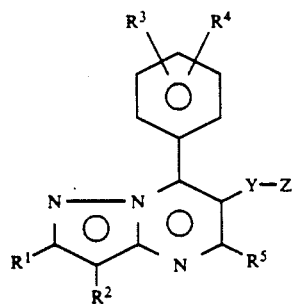
(I)

wherein $R^1$ and $R^2$ are independently hydrogen, $C_{1-8}$ alkyl, $C_{2-6}$ alkenyl, $C_{3-7}$ cycloalkyl, $C_{1-6}$ alkoxy, $C_{1-6}$ alkylthio, fluoro, chloro, bromo,

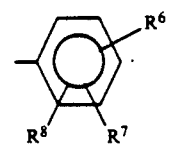

(wherein $R^6$, $R^7$ and $R^8$ are independently hydrogen, $C_{1-4}$ alkyl, $C_{1-3}$ alkoxy, $C_{3-7}$ cycloalkyl, trifluoromethyl, fluoro, chloro or bromo), 2-, 3- or 4-pyridyl, 2- or 5-pyrimidyl, 2- or 3-thienyl, 2- or 3-furyl, α- or β-naphthyl,

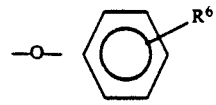

(wherein R⁶ is as defined above),
—NR⁹R¹⁰ (wherein R⁹ and R¹⁰ are independently hydrogen, C₁₋₄ alkyl,

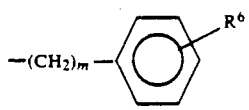

(wherein R⁶ is as defined above, and m is 1, 2 or 3), or R⁹ and R¹⁰ together form —(CH₂)ⱼ—(wherein j is 3, 4 or 5)); or C₁₋₃ alkyl substituted by

(wherein R⁶ is as defined above) and by 0, 1 or 2 members selected from the group consisting of C₁₋₈ alkyl;
R³ and R⁴ are independently hydrogen, C₁₋₈ alkyl, C₃₋₇ cycloalkyl, C₁₋₃ alkoxy, n-butoxy, i-butoxy, sec-butoxy, t-butoxy, R²⁵R²⁶N—(wherein R²⁵ and R²⁶ are independently hydrogen or C₁₋₃ alkyl), trifluoromethyl, trifluoromethoxy, difluoromethoxy, fluoro, chloro, bromo, phenyl, phenoxy, benzyloxy, hydroxy, trimethylsilyloxy, diphenyl-t-butylsilyloxy, hydroxymethyl or —O(CH₂)ₗOR¹⁵ (wherein R¹⁵ is hydrogen or C₁₋₃ alkyl, and l is 1, 2 or 3); or when located at the ortho position to each other, R³ and R⁴ may together form —CH=CH—CH=CH— or methylenedioxy; Y is —CH₂—, —CH₂CH₂—, —CH=CH—, —CH₂—CH=CH—, —CH=CH—CH₂—, —C(CH₃)=CH— or —CH=C(CH₃)—; Z is —Q—CH₂WCH₂—CO₂R¹²,

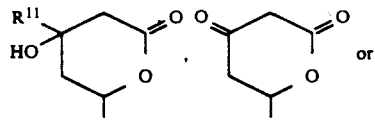

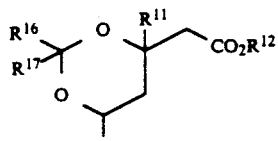

(wherein Q is —C(O)—, —C(OR¹³)₂— or —CH(OH)—; W is —C(O)—, —C(OR¹³)₂— or —C(R¹¹)(OH)—; R¹¹ is hydrogen or C₁₋₃ alkyl; R¹² is hydrogen or R¹⁴ (wherein R¹⁴ is C₁₋₆ alkyl) or M (wherein M is NHR²⁷R²⁸R²⁹ (wherein R²⁷, R²⁸ and R²⁹ are independently hydrogen or C₁₋₄ alkyl) sodium potassium or ½ calcium); each R¹³ are independently primary or secondary C₁₋₆ alkyl; or both R¹³s together form —(CH₂)₂— or —(CH₂)₃—; R¹⁶ and R¹⁷ are independently hydrogen or C₁₋₃ alkyl; or R¹⁶ and R¹⁷ together form —(CH₂)₂— or —(CH₂)₃); and R⁵ is hydrogen, C₁₋₈ alkyl, C₂₋₆ alkenyl, C₃₋₇ cycloalkyl, C₅₋₇ cycloalkenyl, or

(wherein R⁶ is as defined above), or N-C₁₋₃ alkyl substituted by one member selected from the group consisting of

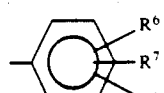

(wherein R⁶, R⁷ and R⁸ are as defined above) and by 0, 1 or 2 members selected from the group consisting of C₁₋₃ alkyl.

2. The compound according to claim 1, wherein in the formula I, R¹ and R² are independently hydrogen, C₁₋₈ alkyl, C₂₋₆ alkenyl, C₃₋₇ cycloalkyl, fluoro, chloro, bromo,

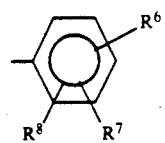

(wherein R⁶, R⁷ are independently hydrogen, C₁₋₄ alkyl, C₁₋₃ alkoxy, C₃₋₇ cycloalkyl, trifluoromethyl, fluoro, chloro, or bromo), 2-, 3- or 4-pyridyl, 2- or 5-pyrimidyl, 2- or 3-thienyl, 2- or 3-furyl, α- or β-naphthyl; or C₁₋₃ alkyl substituted by

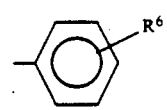

(wherein R⁶ is as defined above) and 0, 1 or 2 members selected from the group consisting of C₁₋₈ alkyl;
R¹ and R⁴ are independently hydrogen, C₁₋₈ alkyl, C₃₋₇ cycloalkyl, C₁₋₃ alkoxy, n-butoxy, i-butoxy, sec-butoxy, t-butoxy, R²⁵R²⁶N—(wherein R²⁵ and R²⁶ are independently hydrogen or C₁₋₃ alkyl), trifluoromethyl, trifluoromethoxy, difluoromethoxy, fluoro, chloro, bromo, phenyl, phenoxy, benzyloxy, hydroxy, trimethylsilyloxy, diphenyl-t-butylsilyloxy, hydroxymethyl or —O(CH₂)ₗOR¹⁵ (wherein R¹⁵ is hydrogen or C₁₋₃ alkyl, and l is 1, 2 or 3); or when located at the ortho position to each other, R³ and R⁴ may together form —CH=CH—CH=CH— or methylenedioxy; Y is —CH₂—, —CH₂CH₂—, —CH=CH—, —CH₂—CH=CH—, —CH=CH—CH₂—, —C(CH₃)=CH— or —CH=C(CH₃)—; Z is —Q—CH₂WCH₂—CO₂R¹²,

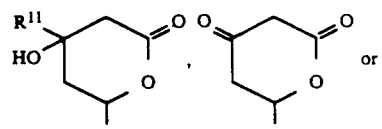

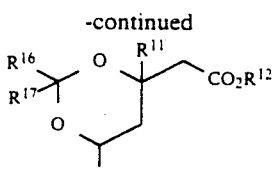

(wherein Q is —C(O)—, —C(OR$^{13}$)$_2$—or —CH(OH)—; W is —C(O)—, —C(OR$^{13}$)$_2$—or —C(R$^{11}$)(OH)—; R$^{11}$ is hydrogen or C$_{1-3}$ alkyl; R$^{12}$ is hydrogen or R$^{14}$ (wherein R$^{14}$ is C$_{1-6}$ alkyl) or M (wherein M is NHR$^{27}$R$^{28}$ R$^{29}$ (wherein R$^{27}$, R$^{28}$ and R$^{29}$ are independently hydrogen or C$_{1-4}$ alkyl), sodium, potassium or ½ calcium); each R$^{13}$ are independently primary or secondary C$_{1-6}$ alkyl; or both R$^{13}$s together form —(CH$_2$)$_2$—or —(CH$_2$)$_2$—; R$^{16}$ and R$^{17}$ are independently hydrogen or C$_{1-3}$ alkyl; or R$^{16}$ and R$^{17}$ together form —(CH$_2$)$_2$-13 or —(CH$_2$)$_3$—); and R$^5$ is hydrogen, C$_{1-8}$ alkyl, C$_{2-6}$ alkenyl, C$_{3-7}$ cycloalkyl, C$_{5-7}$ cycloalkenyl, or

(wherein R$^6$ is as defined above), or n- C$_{1-3}$ alkyl substituted by one member selected from the group consisting of

(wherein R$^6$, R$^7$ and R$^8$ are as defined above) and by 0, 1 or 2 members selected from the group consisting of C$_{1-3}$ alkyl.

3. The compound according to claim 1, wherein in the formula I, R$^1$ and R$^2$ are independently hydrogen, C$_{1-8}$ alkyl, C$_{2-6}$ alkenyl, C$_{3-7}$ cycloalkyl,

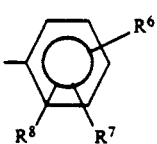

(wherein R$^6$, R$^7$ and R$^8$ are independently hydrogen, C$_{1-4}$ alkyl, C$_{1-3}$ alkoxy, C$_{3-7}$ cycloalkyl, trifluoromethyl, fluoro, chloro or bromo), 2- 3-, or 4-pyridyl, 2- or 5-pyrimidyl, 2- or 3-thienyl, 2- or 3-furyl, α- or β-naphthyl or C$_{1-3}$ alkyl substituted by

(wherein R$^6$ is as defined above), and by 0, 1 to 2 members selected from the group consisting of C$_{1-8}$ alkyl;
R$^3$ and R$^4$ are independently hydrogen, C$_{1-8}$ alkyl, C$_{1-3}$ alkoxy, n-butoxy, i-butoxy sec-butoxy, t-butoxy, trifluoromethyl, fluoro, chloro, bromo, phenoxy, benzyloxy, hydroxy, trimethylsilyloxy, diphenyl-t-butylsilyloxy, hydroxmethyl or —O(CH$_2$)$_l$OR$^{15}$ (wherein R$^{15}$ is hydrogen or C$_{1-3}$ alkyl, and l is 1, 2 or 3); or when located at the ortho position to each other, R$^3$ and R$^4$ may together form methylenedioxy; Y is —CH$_2$CH$_2$—or —CH=CH—; Z is —Q—CH$_2$WCH$_2$—CO$_2$R$^{12}$,

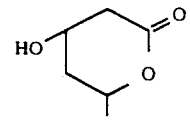

(wherein Q is —C(O)—or —CH(OH)—; W is —C(O)—or —CH(OH)—; R$^{12}$ is as defined in claim 1; and R$^5$ is C$_{1-8}$ alkyl, C$_{2-6}$ alkenyl or C$_{3-7}$ cycloalkyl.

4. The compound according to claim 1, wherein in the formula I, R$^1$ and R$^2$ are independently hydrogen, C$_{1-8}$ alkyl, C$_{2-6}$ alkenyl, C$_{3-7}$ cycloalkyl or

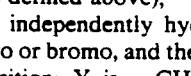

(wherein R$^6$, R$^7$ and R$^8$ are independently hydrogen, C$_{1-4}$ alkyl, C$_{1-3}$ alkoxy, C$_{3-7}$ cycloalkyl, trifluoromethyl, fluoro, chloro or bromo) or C$_{1-3}$ alkyl unsubstituted or substituted by 1 or 2 members selected from the group consisting of (wherein R$^6$ is as defined above);
R$^3$ and R$^4$ are independently hydrogen, C$_{1-8}$ alkyl, fluoro, chloro or bromo, and they are located at the 3- and 4-position; Y is —CH$_2$CH$_2$—or —CH=CH—; Z is —Q—CH$_2$WCH$_2$—CO$_2$R$^{12}$,

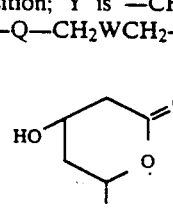

(wherein Q is —C(O)—or —CH(OH)—; W is —C(O)—or —CH(OH)—; R$^{12}$ is as defined in claim 1; and R$^5$ is ethyl, n-propyl, i-propyl or cyclopropyl.

5. The compound according to claim 1, wherein in the formula I, R$^1$ and R$^2$ are independently hydrogen, methyl, ethyl, n-propyl, i-propyl, n-butyl, i-butyl, sec-butyl, t-butyl, n-pentyl, i-pentyl, 1,2-dimethylpentyl, n-hexyl, vinyl, n-propenyl, i-propenyl, cyclopropyl, cyclobutyl, cyclohexyl, phenyl, 2-methylphenyl, 3-methylphenyl, 4-methylphenyl, 2-chlorophenyl, 3-chlorophenyl, 4-chlorophenyl, 2-methylphenyl, 3-methoxyphenyl, 4-methoxyphenyl, 3,4-dimethylphenyl, 3,4-dichlorophenyl, 3-trifluoromethylphenyl, benzyl, 4-chlorobenzyl, 4-methylbenzyl, 4-methyoxybenzyl, 2-phenethyl when R$^4$ is hydrogen, R$^3$ is hydrogen, 3-methyl, 4-methyl, 3-chloro, 4-chloro, 3-fluoro or 4fluoro; or R$^3$ and R$^4$ together form 3-methyl-4-chloro, 3,5-dichloro, 3,5-difluoro, 3,5-dimethyl or 3-methyl-4fluoro; Y is —CH$_2$CH$_2$— or —CH=CH—; Z is —Q—CH$_2$WCH$_2$—CO$_2$R$^{12}$,

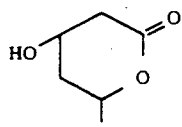

(wherein Q is —C(O)— or —CH(OH)—; W is —C(O)— or —CH(OH)—R$^{12}$ is as defined in claim 1; and R$^5$ is i-propyl or cyclopropyl.

6. The compound according to claim 1, wherein in the formula I, R$^1$, R$^2$, R$^3$, R$^4$, Y and Z are as defined in claim 1; and R$^5$ is cyclopropyl.

7. The compound according to claim 1, which is (E)-7-[7'-(4''-fluorophenyl)-2'-methyl-5'-(1''-methylethyl)pyrazolo[1,5-a]pyrimidin-6'-yl]-3,5-dihydroxyhept-6 enoic acid, a sodium salt, methyl ester, ethyl ester, n-propyl ester or i-propyl ester of the carboxylic acid, or a lactone formed by the condensation of the carboxylic acid with hydroxy at the 5-position.

8. The compound according to claim 1, which is (E) 7-[2'-t-butyl-7'-(4''-fluorophenyl)-5'-(1''-methylethyl)-pyrazolo[1,5-a]pyrimidin-6'-yl]-3,5-dihydroxyhept-6-enoic acid, a sodium salt, methyl ester, ethyl ester, n-propyl ester or i-propyl ester of the carboxylic acid, or a lactone formed by the condensation of the carboxylic acid with hydroxy at the 5-position.

9. The compound according to claim 1, which is (E)-7-[7'-(4''-fluorophenyl)-5'-(1''-methylethyl)-2'-phenylpyrazolo[1,5-a]pyrimidin-6'-yl]-3,5-dihydroxyhept-6-enoic acid, a sodium salt, methyl ester, ethyl ester, n-propyl ester or i-propyl ester of the carboxylic acid, or a lactone formed by the condensation of the carboxylic acid with hydroxy at the 5-position.

10. The compound according to claim 1, which is (E)-7-[5'-cyclopropyl-7'-(4''-fluorophenyl)-2'-methyl-pyrazolo[1,5-a]pyrimidin-6'-yl]-3,5-dihydroxyhept-6-enoic acid, a sodium salt, methyl ester, ethyl ester, n-propyl ester or i-propyl ester of the carboxylic acid, or a lactone formed by the condensation of the carboxylic acid with hydroxy at the 5-position.

11. The compound according to claim 1, which is (E)-7-[5'-cyclopropyl-7'-(4''-fluorophenyl)-2',3'-dimethylpyrazolo[1,5-a]pyrimidin-6'-yl]-3,5-dihydroxyhept 6-enoic acid, a sodium salt, methyl ester, ethyl ester, n-propyl ester or i-propyl ester of the carboxylic acid, or a lactone formed by the condensation of the carboxylic acid with hydroxy at the 5-position.

12. The compound according to claim 1, which is (E)-7-[5'-cyclopropyl-7'-(4''-fluorophenyl)-2'-methyl-3'-phenylpyrazolo[1,5-a]pyrimidin-6'-yl]-3,5-dihydroxyhept-6-enoic acid, a sodium salt, methyl ester, ethyl ester, n-propyl ester or i-propyl ester of the carboxylic acid, or a lactone formed by the condensation of the carboxylic acid with hydroxy at the 5-position.

13. The compound according to claim 1, which is (E)-7-[7'-(4''-fluorophenyl)-2'-(2''-furyl)-5'-(1''-methylethyl)pyrazolo[1,5-a]pyrimidin-6,-yl]-3,5-dihydroxyhept-6-enoic acid, a sodium salt, methyl ester, ethyl ester, n-propyl ester or i-propyl ester of the carboxylic acid, or a lactone formed by the condensation of the carboxylic acid with hydroxy at the 5-position.

14. The compound according to claim 1, which is (E)-7-[5'-cyclopropyl-7'-(4''-fluorophenyl)-2'-(1''-methylethyl)pyrazolo[1,5-a]pyrimidin-6'-yl]-3,5-dihydroxyhept-6-enoic acid, a sodium salt, methyl ester, ethyl ester, n-propyl ester or i-propyl ester of the carboxylic acid, or a lactone formed by the condensation of the carboxylic acid with hydroxy at the 5-position.

15. An anti-hyperlipidemia agent containing a pharmaceutically effective amount of the compound of the formula I as defined in claim 1 and a pharmaceutically acceptable carrier.

16. An anti-hyperlipoproteinemia agent containing a pharmaceutically effective amount of the compound of the formula I as defined in claim 1 and a pharmaceutically acceptable carrier.

17. An anti-atherosclerosis agent containing a pharmaceutically effective amount of the compound of the formula I as defined in claim 1 and a pharmaceutically acceptable carrier.

18. A method for reducing hyperlipidemia, hyperlipoproteinemia or atherosclerosis, which comprises administering an effective amount of the compound of the formula I as defined in claim 1.

* * * * *